United States Patent
Uchida et al.

(10) Patent No.: US 12,048,417 B2
(45) Date of Patent: Jul. 30, 2024

(54) EXTERNAL MECHANISM FOR ENDOSCOPE, AND ENDOSCOPE APPARATUS

(71) Applicant: OLYMPUS CORPORATION, Tokyo (JP)

(72) Inventors: Ramiya Uchida, Tachikawa (JP); Masanobu Koitabashi, Hachioji (JP); Yasuhiro Okamoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 929 days.

(21) Appl. No.: 17/097,271

(22) Filed: Nov. 13, 2020

(65) Prior Publication Data
US 2021/0063723 A1    Mar. 4, 2021

Related U.S. Application Data

(63) Continuation of application No. PCT/JP2019/006619, filed on Feb. 21, 2019.

(30) Foreign Application Priority Data

May 24, 2018  (JP) ................... 2018-099601

(51) Int. Cl.
*A61B 1/00* (2006.01)
*A61B 1/005* (2006.01)
*G02B 23/24* (2006.01)

(52) U.S. Cl.
CPC ...... *A61B 1/00133* (2013.01); *A61B 1/00042* (2022.02); *A61B 1/005* (2013.01); *G02B 23/2461* (2013.01); *G02B 23/2476* (2013.01); *A61B 1/0016* (2013.01)

(58) Field of Classification Search
CPC . A61B 1/00133; A61B 1/00042; A61B 1/005; A61B 1/0016; A61B 1/0052; G02B 23/2461; G02B 23/2476
See application file for complete search history.

(56) References Cited

U.S. PATENT DOCUMENTS

2007/0232856 A1  10/2007  Ueno et al.
2010/0268031 A1  10/2010  Koyama

FOREIGN PATENT DOCUMENTS

| EP | 1 825 801 A1 | 8/2007 |
| JP | 03-097429 A | 4/1991 |
| JP | 05-300873 A | 11/1993 |

(Continued)

OTHER PUBLICATIONS

International Search Report dated May 28, 2019 received in PCT/JP2019/006619.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An external mechanism for endoscope includes a bending wheel, a motor, a housing case, and an operation switch, a case side fitting surface and a switch side fitting surface are formed flat to each other, and when a protrusion is provided on a contact surface of the housing case, a recess is provided on a contact surface of the operation switch, whereas when a protrusion is provided on the contact surface of the operation switch, a recess is provided on the contact surface of the housing case.

14 Claims, 20 Drawing Sheets

(56) References Cited

FOREIGN PATENT DOCUMENTS

| | | | | |
|---|---|---|---|---|
| JP | H05300873 | A | * | 11/1993 |
| JP | 06-254047 | A | | 9/1994 |
| JP | H06254047 | A | * | 9/1994 |
| JP | 2008-048788 | A | | 3/2008 |
| JP | 2011018016 | A | * | 1/2011 |
| WO | 2006/059722 | A1 | | 6/2006 |
| WO | 2010/047223 | A1 | | 4/2010 |

* cited by examiner

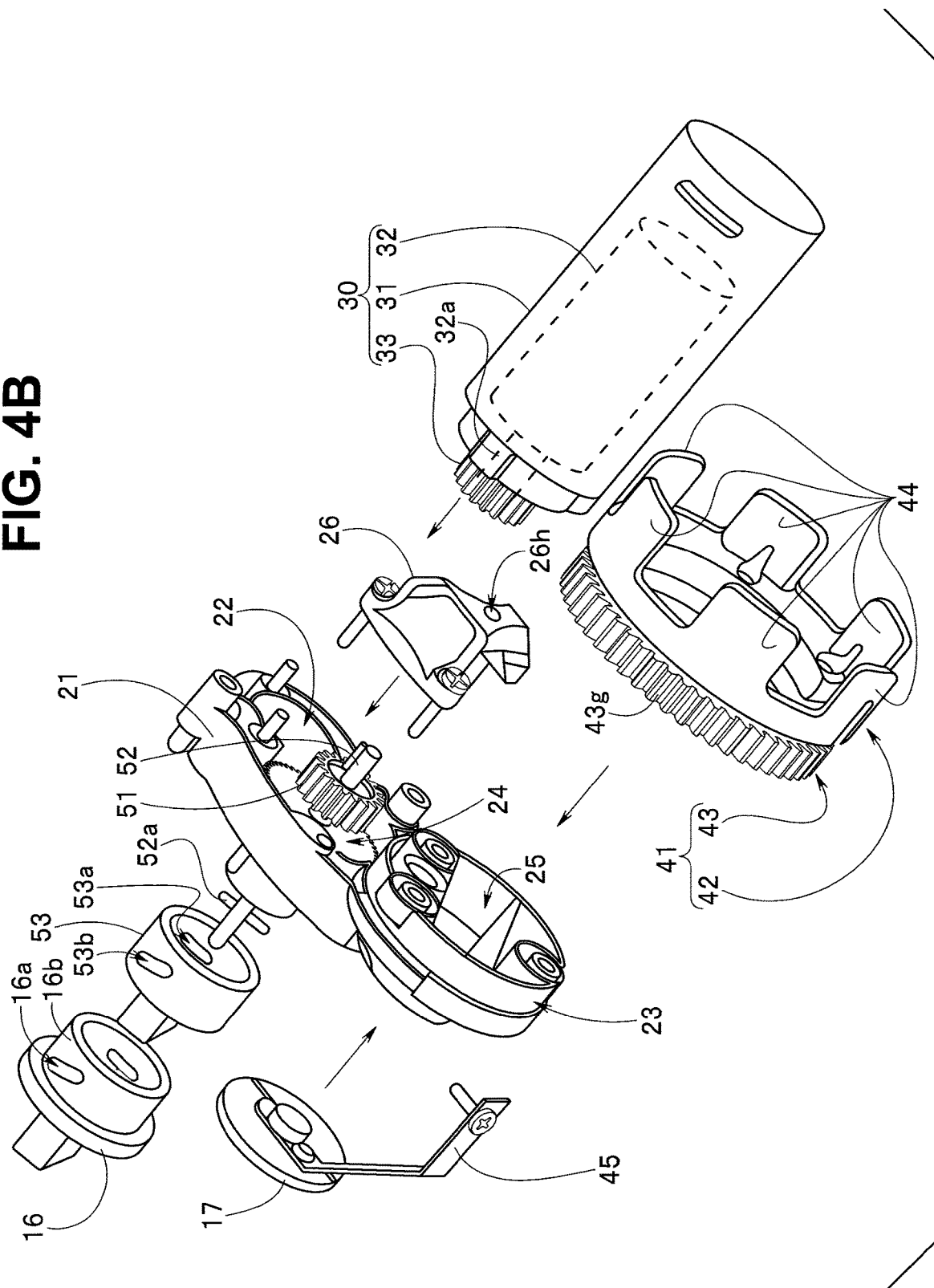

EXTERNAL MECHANISM FOR ENDOSCOPE, AND ENDOSCOPE APPARATUS

CROSS REFERENCE TO RELATED APPLICATION

This application is a continuation application of PCT/JP2019/006619 filed on Feb. 21, 2019 and claims benefit of Japanese Application No. 2018-099601 filed in Japan on May 24, 2018, the entire contents of which are incorporated herein by this reference.

BACKGROUND OF THE INVENTION

1. Field of the Invention

The present invention relates to an external mechanism for endoscope, and an endoscope apparatus that rotate a bending operation knob with a driving force by attaching an external unit including an operation switch to the bending operation knob of an endoscope, and bend a bending portion provided at an insertion portion.

2. Description of the Related Art

Endoscopes are used in the medical field, the industrial field and the like. An endoscope includes a bending portion at an elongated insertion portion that is inserted into a subject or an object.

Japanese Patent Application Laid-Open Publication No. H05-300873 discloses a configuration of a bending control apparatus for endoscope that enables a manual angle type endoscope to be also usable as an electrical angle control type endoscope. The manual angle type endoscope can orient an endoscope distal end portion in a desired direction by rotating a UD angle knob and an RL angle knob that are located at one side of an operation portion by a manual operation, and bending an endoscope bending portion in an arbitrary direction.

The aforementioned bending control apparatus for endoscope includes a UD angle knob driving motor, and an RL angle knob driving motor, in a main body portion, and a UD angle switch and an RL angle switch are provided at a side part of the main body portion.

The main body portion is attachable to and detachable from an operation portion, and in a state where the main body portion is fixed to the operation portion, engaging portions provided at the respective angle knob driving motors are engaged with respective angle knobs.

In the configuration like this, a user operates the respective angle switches to cause the respective angle knob driving motors to rotate forward, rotate reversely, or stop, and thereby operates the respective angle knobs to orient an endoscope distal end portion in a desired direction.

Japanese Patent Application Laid-Open No. 2008-48788 discloses an endoscope in which a first bending portion and a second bending portion that are arranged in parallel in an extending direction of an insertion portion are included at a distal end side of the elongated insertion portion, and a main bending operation apparatus and a sub bending operation apparatus are provided in an operation portion located at a proximal end side of the insertion portion.

In the endoscope like this, a bending operation of the first bending portion is performed by rotationally operating an operation knob of the main bending operation apparatus, and a bending operation of the second bending portion is performed by rotationally operating an operation knob of the sub bending operation apparatus.

Accordingly, it is possible for a user to bend the first bending portion or the second bending portion by rotationally operating each of the operation knobs independently.

As a result, it is possible for the user to insert the insertion portion smoothly into a lumen that is bent complicatedly, or to easily direct an observation optical system contained at a distal end side of the insertion portion in a desired direction.

Here, in the operation portion of the endoscope described above, the sub bending operation apparatus is provided at a proximal end side of the operation portion at an opposite side to the insertion portion from the main bending operation apparatus by being separated from the main bending operation apparatus.

There is also known an external electric bending mechanism that is attachable to and a detachable from an operation portion, and in an attached state, rotates, for example, a sub bending operation apparatus by a driving force of a driving source such as a motor.

In the aforementioned external electric bending mechanism, an operation switch for operating the driving source is necessary in the state of the external electric bending mechanism being attached to the operation portion. It is conceivable to provide an angle switch as disclosed in Japanese Patent Application Laid-Open Publication No. H05-300873 at a main body portion side part of the external electric bending mechanism as the operation switch.

SUMMARY OF THE INVENTION

An external mechanism for endoscope according to one aspect of the present invention includes an engaging member configured to engage with an operation knob of a bending operation apparatus provided at an operation portion of an endoscope, a driving source configured to generate a driving force for rotating the engaging member, a housing case configured to house the engaging member and the driving source, and to be attached to the operation portion attachably and detachably, and an operation switch configured to be attachably and detachably fitted to an outer portion of the housing case, and to output a control signal to the driving source by an operation element being operated, wherein respective contact surfaces that contact each other in a fitting state of the housing case and the operation switch are formed flat to each other, when a protrusion that protrudes toward the contact surface of the operation switch is provided on the contact surface of the housing case, a recess in which the protrusion engages is provided on the contact surface of the operation switch, and when a protrusion that protrudes toward the contact surface of the housing case is provided on the contact surface of the operation switch, a recess in which the protrusion engages is provided on the contact surface of the housing case.

An endoscope apparatus according to one aspect of the present invention includes the external mechanism for endoscope, and an endoscope.

BRIEF DESCRIPTION OF THE DRAWINGS

FIG. 4B is an exploded perspective view explaining an outline of a configuration of the knob rotation mechanism;

FIG. 10G is a view explaining a state where an engaging distal end portion rotates locking pieces against urging forces of urging members following movement of the operation switch;

FIG. 10H is a view explaining a state where abutting proximal end surfaces of the engaging distal end portion abut on one side surfaces of the locking pieces, and the other side surfaces of the locking pieces abut on holding surfaces of holding portions, thereby the operation switch and the housing case are integrally fixed;

FIG. 10I is a view illustrating a state in which the operation switch is moved with respect to the housing case to release the integrally fixed state and the locking pieces are moved onto inclined surfaces; and FIG. 10J is a view explaining a state where the column protruded portion of the housing case is pulled out of the locking hole of the operation switch, the locking pieces cannot return to a state where the locking pieces are urged by the urging members, and reengagement is hindered.

DETAILED DESCRIPTION OF THE PREFERRED EMBODIMENT

Figure 1:
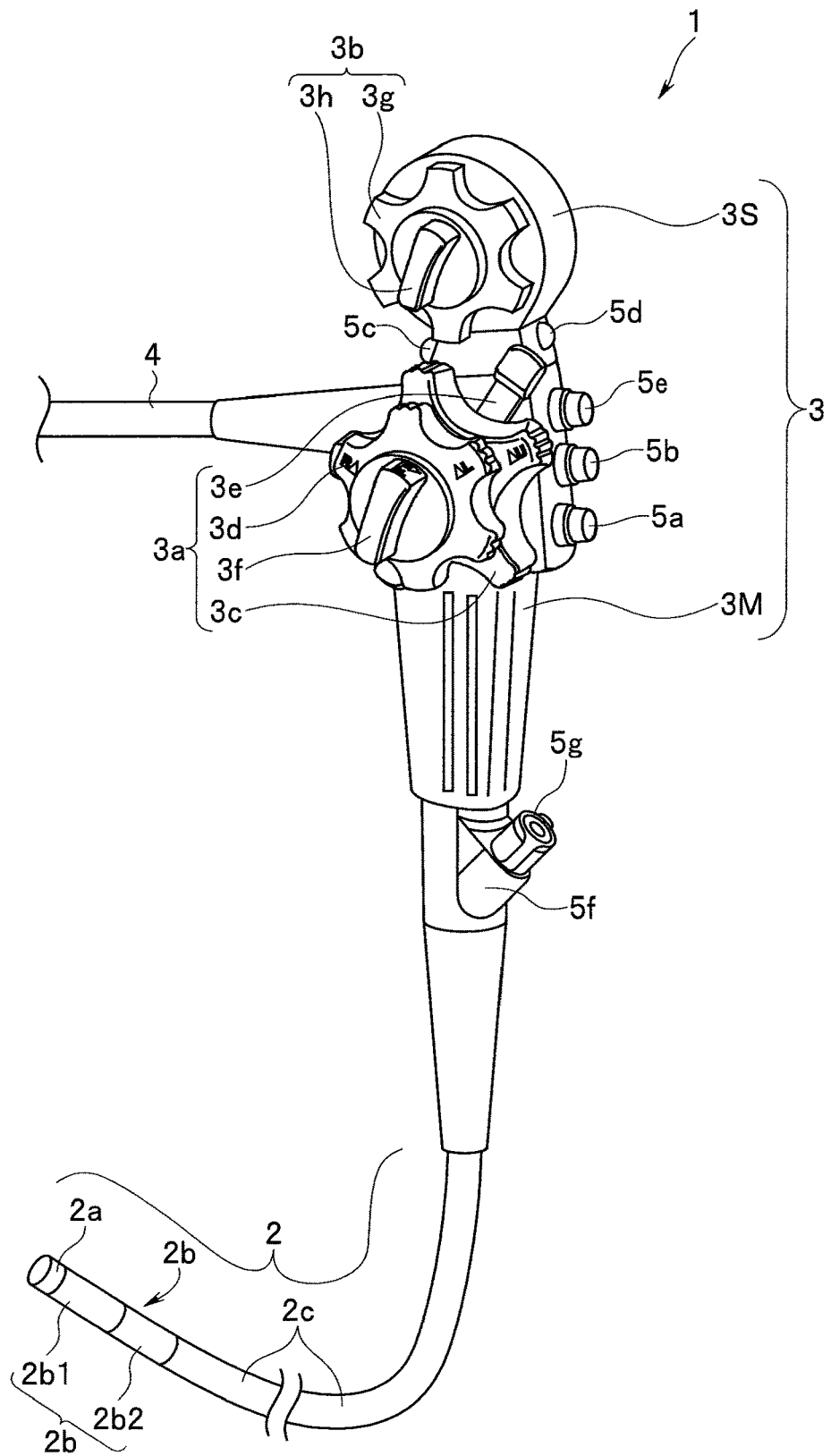
FIG. 1 is a view explaining an endoscope including a sub operation portion.

Hereinafter, an embodiment of the present invention will be described with reference to the drawings. Note that in respective drawings that are used in the following explanation, a scale may differ for each of components so that the respective components have such sizes that the respective components are recognizable on the drawings. In other words, the present invention is not limited only to numbers and quantities of the components, shapes of the components, ratios of sizes of the components, and relative positional relationship of the respective components that are illustrated in the drawings.

A configuration of an endoscope will be described with reference to FIG. 1.

An endoscope 1 illustrated in FIG. 1 includes an elongated insertion portion 2, an operation portion 3 also serving as a grasping portion, and a universal cord 4.

The insertion portion 2 is configured by a distal end portion 2a, a bending portion 2b, and a long flexible tube portion 2c having flexibility being connectively provided in order from a distal end side of the insertion portion 2.

In the present embodiment, the bending portion 2b has a first bending portion 2b1, and a second bending portion 2b2.

The first bending portion 2b1 is provided at a distal end side of the insertion portion 2. The second bending portion 2b2 is provided connectively to a proximal end portion of the first bending portion 2b1 via a connecting portion (not illustrated).

The first bending portion 2b1 is bendable in up-down and left-right directions, for example. In contrast with this, the second bending portion 2b2 is bendable in the up-down direction.

The operation portion 3 has a first bending operation apparatus 3a, and a second bending operation apparatus 3b.

In the present embodiment, the operation portion 3 has a main operation portion 3M and a sub operation portion 3S. The main operation portion 3M also serves as a grasping portion and is provided with the first bending operation apparatus 3a. The sub operation portion 3S is provided at a proximal end side of the main operation portion 3M and is provided with the second bending operation apparatus 3b.

The second bending operation apparatus 3b is provided at an operation portion proximal end side that is separated from the first bending operation apparatus 3a and is an opposite side to the insertion portion 2.

The first bending operation apparatus 3a has a first bending portion up-down operation knob (hereinafter, abbreviated as a first UD knob) 3c and a first bending portion left-right operation knob (hereinafter, abbreviated as a first RL knob) 3d as bending operation knobs, and a first bending portion up-down direction fixing lever (hereinafter, abbreviated as a first UD fixing lever) 3e and a first bending portion left-right direction fixing tab (hereinafter, abbreviated as a first RL fixing tab) 3f.

The second bending operation apparatus 3b has a second bending portion up-down operation knob (hereinafter, abbreviated as a second UD knob) 3g that is a bending operation knob, and a second bending portion up-down direction fixing tab (hereinafter, abbreviated as a second UD fixing tab) 3h.

The first UD knob 3c is rotated when the first bending portion 2b1 is operated to bend in the up-down direction. The first RL knob 3d is rotated when the first bending portion 2b1 is operated to bend in the left-right direction.

The first UD fixing lever 3e is switchable to a free position and a fixing position. The first RL fixing tab 3f is switchable to a free position and a fixing position.

When the first UD fixing lever 3e is in the free position, the first UD knob 3c is rotationally operable. At this time, the first bending portion 2b1 is in a state where the first bending portion 2b1 bends in an up direction or a down direction with the rotational operation of the first bending portion up-down knob 3c.

When the first RL fixing tab 3f is in the free position, the first RL knob 3d is rotationally operable. At this time, the first bending portion 2b1 is in a state where the first bending portion 2b1 bends in a left direction or a right direction with the rotational operation of the first RL knob 3d.

In contrast with this, when the first UD fixing lever 3e is switched to the fixing position, rotation of the first UD knob 3c is restricted.

As a result, a bending state in the up-down direction of the first bending portion 2b1 is held in a state at a switching time. Similarly, when the first RL fixing tab 3f is switched to the fixing position, rotation of the first RL knob 3b is restricted. As a result, a bending state in the left-right direction of the first bending portion 2b1 is held in a state at a switching time.

The second UD knob 3g is rotated when the second bending portion 2b2 is operated to bend in the up-down direction. The second UD fixing tab 3h is switchable to a free position and a fixing position.

When the second UD fixing tab 3h is in the free position, the second UD knob 3g is rotationally operable. At this time, the second bending portion 2b2 is in a state where the second bending portion 2b2 bends in the up direction or the down direction with the rotational operation of the second UD knob 3g.

In contrast with this, when the second UD fixing tab 3h is switched to the fixing position, rotation of the second UD knob 3g is restricted. As a result, a bending state in the up-down direction of the second bending portion 2b2 is held in a state at a switching time.

Note that reference sign 5a denotes a gas-feeding and water-feeding button, reference sign 5b denotes a suction operation button, reference signs 5c, 5d and 5e denote remote switches, reference sign 5f denotes a treatment instrument insertion port, and reference sign 5g denotes a forceps plug.

The remote switches are switches for performing stop or record of an endoscope image displayed on a screen of a display apparatus (not illustrated), enlargement of the image, switching of an illumination light and the like, and optimum functions are assigned to the respective switches.

Figure 2A:
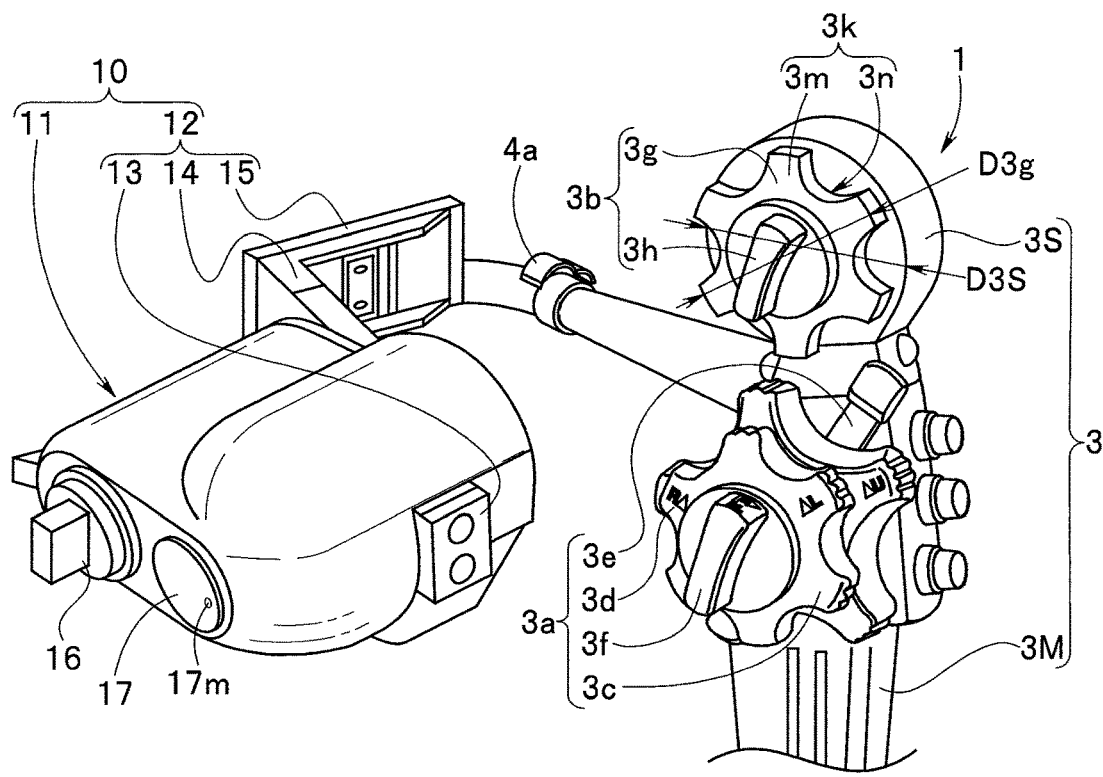
FIG. 2A is a view explaining a relationship between the sub operation portion included by the endoscope and an external mechanism for endoscope.

Reference sign 10 in FIG. 2A denotes an external mechanism for endoscope. The external mechanism 10 for endoscope is attachable to and detachable from the second UD knob 3g provided at the sub operation portion 3S.

The external mechanism 10 for endoscope is an auxiliary mechanism unit that is attached to the second UD knob 3g and rotates the second UD knob 3g with a driving force of a motor (refer to reference sign 32 in FIG. 4B) described later.

Reference sign 11 denotes a housing case, and reference sign 12 denotes a case attaching, detaching and fixing portion (hereinafter, described as a case attaching and detaching portion). The case attaching and detaching portion 12 includes a locking portion 13, a hinge portion 14, and a locking claw portion 15.

The locking portion 13 is fixedly provided at a predetermined position of the housing case 11. The hinge portion 14 is in a substantially L-shape, and has one end portion rotatably placed at a predetermined position of the housing case 11. The locking claw portion 15 is provided at the other end of the L-shaped hinge portion 14.

The hinge portion 14 has a rotating state restricted by engaging and fixing the locking claw portion 15 to the locking portion 13. Reference sign 16 denotes a switching tab, and reference sign 17 denotes a bending state display portion. The bending state display portion 17 includes a rotation index 17m.

Figure 2B:
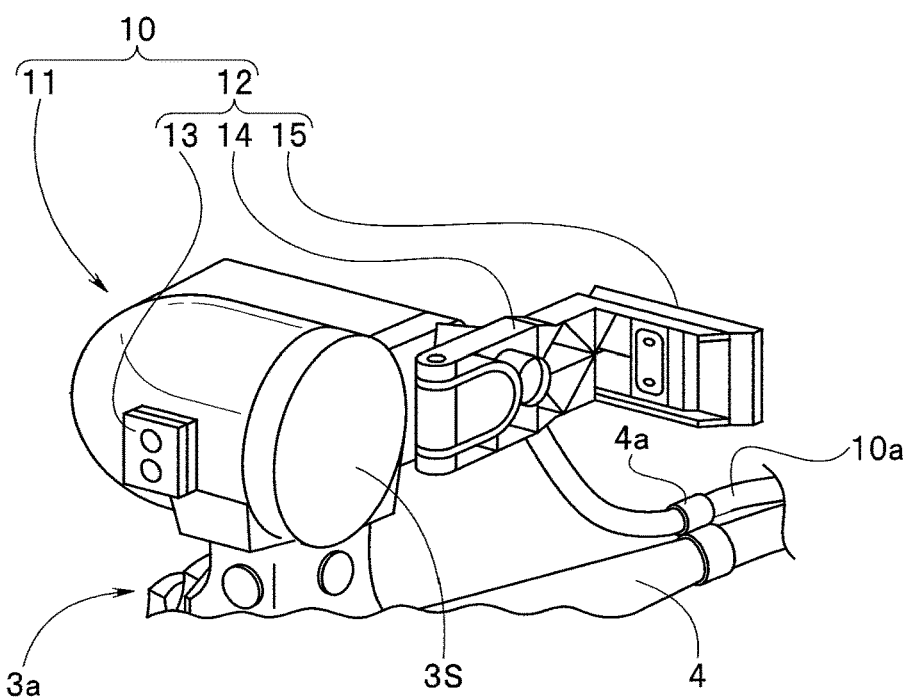
FIG. 2B is a view explaining a state in which the external mechanism for endoscope is disposed at the sub operation portion.

Reference sign 4a denotes a cable attaching tool, and one, or two or more cable attaching tools are provided at a desired position of the universal cord 4 as illustrated in FIG. 2B.

To the cable attaching tool 4a, a signal cable 10a extending from the external mechanism 10 for endoscope is attached.

Figure 2C:
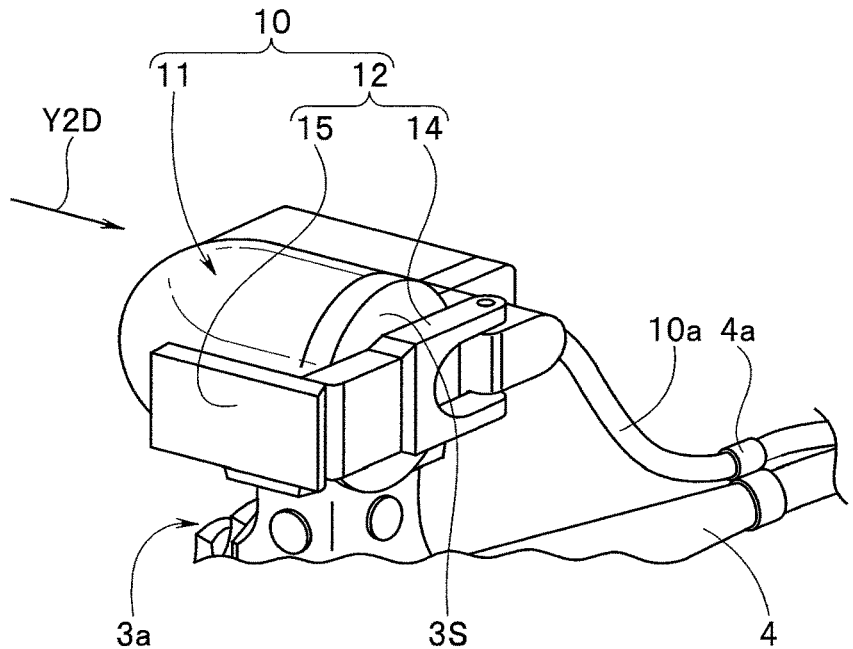
FIG. 2C is a view illustrating a state where the external mechanism for endoscope is attached to the sub operation portion.
Figure 2D:
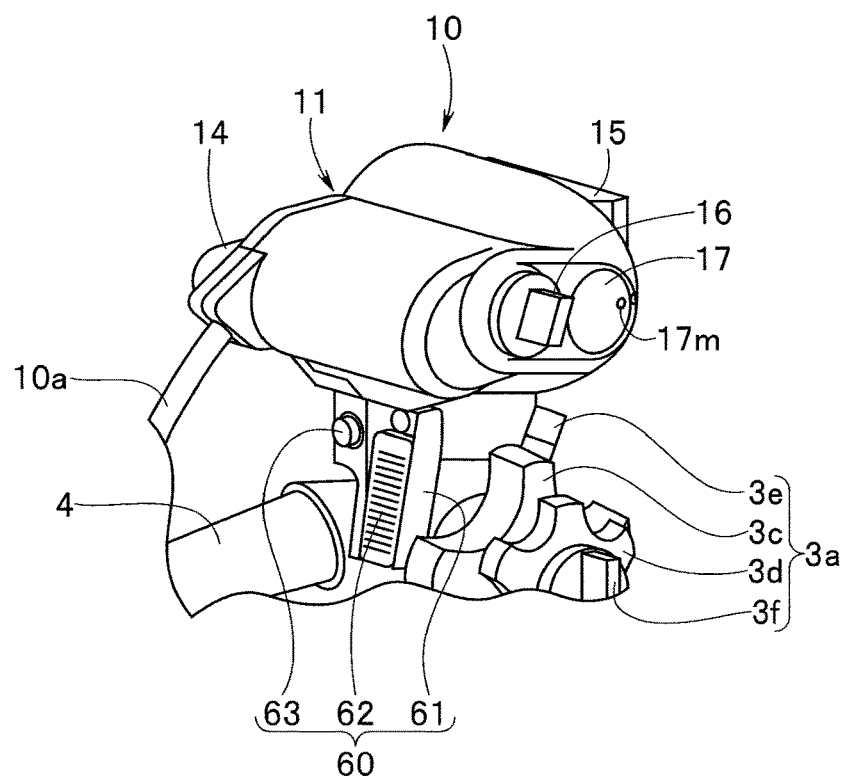
FIG. 2D is a view of the sub operation portion in FIG. 2C seen in an arrow Y2D direction.

The external mechanism 10 for endoscope is integrally attached to the sub operation portion 3S by engaging and fixing the locking claw portion 15 to the locking portion 13 by rotating the locking claw portion 15 with one end portion side of the hinge portion 14 as a fulcrum as illustrated in FIG. 2C and FIG. 2D, in a state where the housing case 11 covers the second UD knob 3g and the housing case 11 is placed on the sub operation portion 3S as illustrated in FIG. 2B.

Note that reference sign 60 in FIG. 2D is an operation switch. The operation switch 60 has a switch case 61, an operation element 62, and a dummy switch 63.

Next, a configuration of the external mechanism 10 for endoscope will be described.

Figure 3:
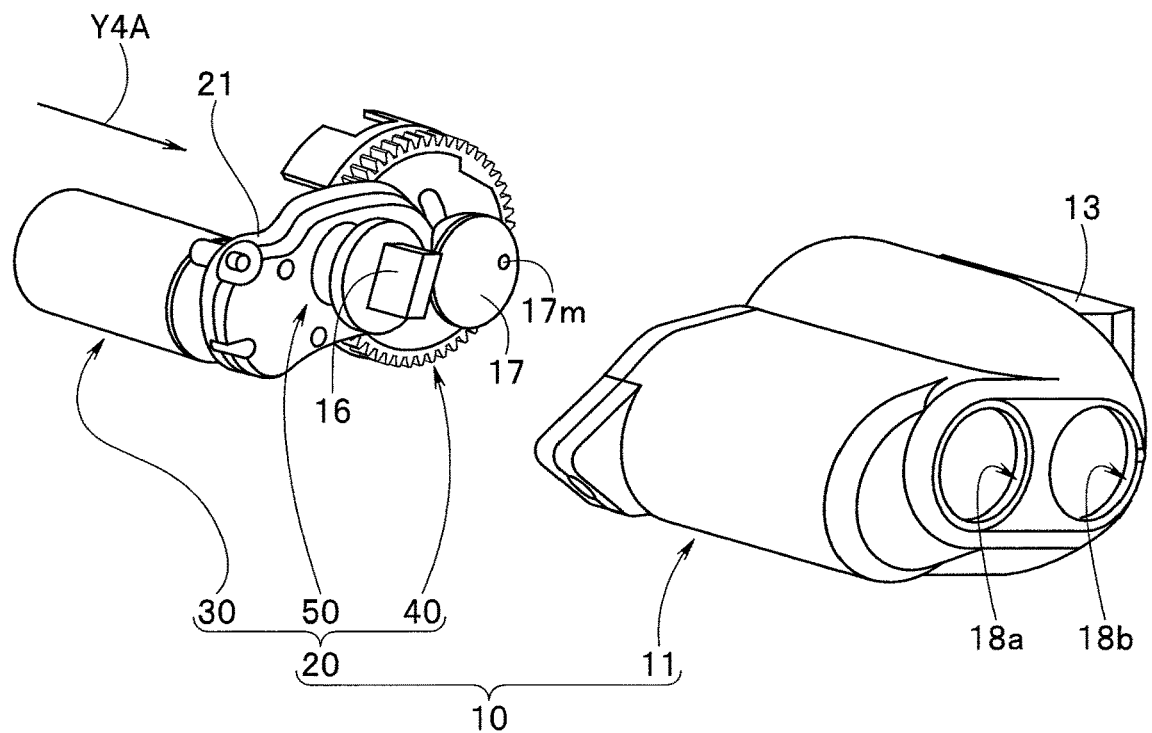
FIG. 3 is a view explaining a relationship between a housing case of the external mechanism for endoscope, and a knob rotation mechanism that is housed in a housing case.

As illustrated in FIG. 3, the external mechanism 10 for endoscope is configured by housing a knob rotation mechanism 20 in a case internal space of the housing case 11.

In the housing case 11, a first through-hole 18a, and a second through-hole 18b are provided. The switching tab 16 is placed in the first through-hole 18a, and the bending state display portion 17 is placed in the second through-hole 18b. The through-holes 18a and 18b cause the case internal space and an outside to communicate with each other.

The knob rotation mechanism 20 will be described with reference to FIG. 3, FIG. 4A, and FIG. 4B.

As illustrated in FIG. 3, the knob rotation mechanism 20 mainly includes a motor portion 30, a knob rotation portion 40, and a transmission portion 50. Reference sign 21 shown in FIG. 3 to FIG. 4B denotes a rotation mechanism portion main body and an attaching member.

As illustrated in FIG. 4B, in the rotation mechanism portion main body 21, a motor attaching portion 22, a wheel attaching portion 23, a switching gear attaching portion 24, and the like are respectively provided in predetermined positions.

Reference sign 25 is a recess for tab. The recess 25 for tab is a hole with an outer shape and a depth formed so that the second UD fixing tab 3h is housed in the hole.

Reference sign 26 is a switching gear support member. The switching gear support member 26 has a through-hole 26h in which one end portion of a switching gear shaft 52 is placed. A switching gear 51 is fixedly provided at the switching gear shaft 52.

The switching gear support member 26 is fixedly provided at a predetermined position of the rotation mechanism portion main body 21. The fixedly provided switching gear support member 26 axially supports one end portion of the switching gear shaft 52 placed in the through-hole 26h rotatably.

The motor portion 30 mainly has a motor case 31, a motor 32 that is a driving source shown by a broken line, and a driving gear 33.

The motor 32 is placed in the motor case 31. The driving gear 33 is fixedly provided on a motor shaft 32a protruding from the motor 32.

Figure 4A:
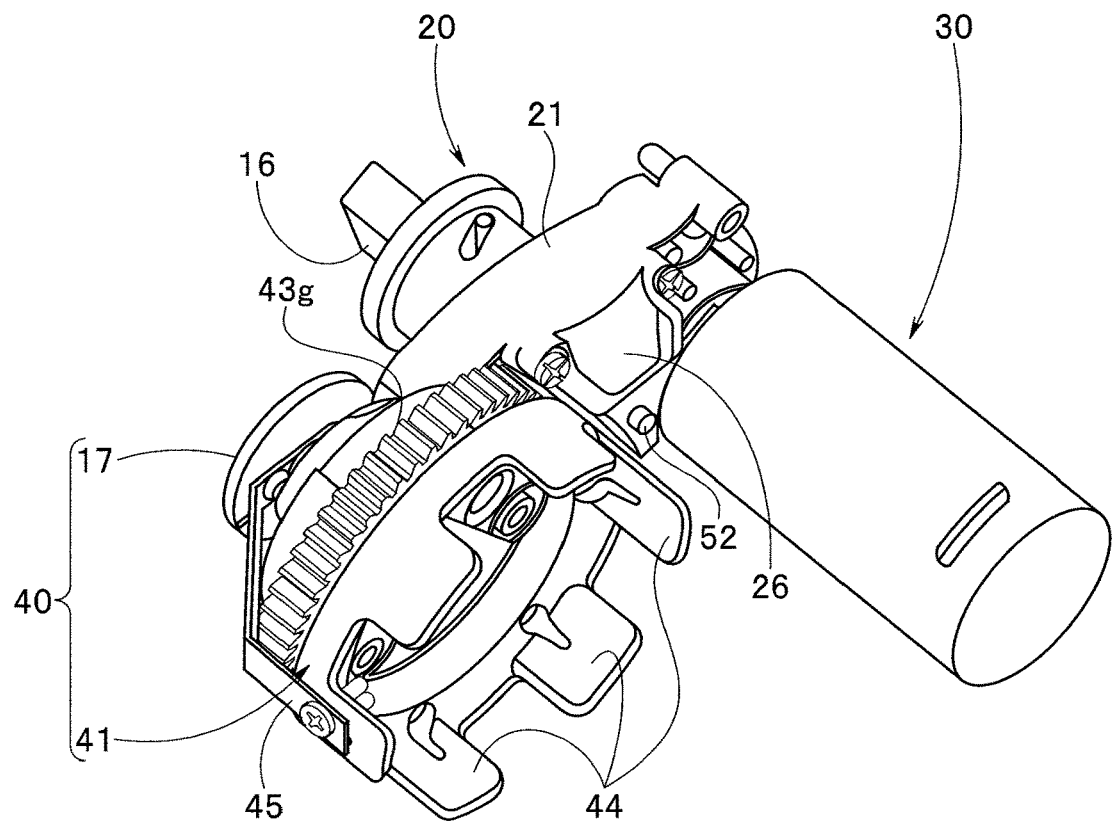
FIG. 4A is a view of the knob rotation mechanism seen in an arrow Y4A direction in FIG. 3.

The motor case 31 is fixedly provided at the motor attaching portion 22, in a predetermined state as illustrated in FIG. 4A.

As illustrated in FIG. 4A and FIG. 4B, the knob rotation portion 40 has a bending wheel 41, and the bending state display portion 17.

The bending wheel 41 has a knob connection portion 42 and a meshing portion 43. The knob connection portion 42 is a ring-shaped member. The knob connection portion 42 and the meshing portion 43 are integrally fixed.

The meshing portion 43 is a gear portion having a gear 43g on an outer peripheral surface. At the knob connection portion 42, a plurality of protruded portions 44 are arranged in a circumferential direction.

The plurality of protruded portions 44 are respectively housed in recesses 3n located among protruded portions 3m, of recesses and protruded portions (reference sign 3k in FIG. 2A) of the second UD knob 3g.

The protruded portions 44 are respectively placed in the recesses 3m, and thereby the second UD knob 3g and the bending wheel 41 are integrated. In the integrated state, the second UD knob 3g is rotated in a rotational direction of the bending wheel 41 with rotation of the bending wheel 41. The bending wheel 41 is an engaging member that is engaged with the second UD knob 3g and is integrated with the second UD knob 3g.

As illustrated in FIG. 3, FIG. 4A and FIG. 4B, the bending state display portion 17 is a disk. As illustrated in FIG. 3, the rotation index 17m is provided in a predetermined position on a disk surface of the bending state display portion 17.

Reference sign 45 in FIG. 4A and FIG. 4B denotes a connection member. As illustrated in FIG. 4B, one end portion of the connection member 45 is integrally provided fixedly on a disk back surface of the bending state display portion 17.

As illustrated in FIG. 4A, the other end portion of the connection member 45 is integrally provided fixedly at a predetermined position on an outer peripheral surface of the knob connection portion 42 included by the bending wheel 41.

Accordingly, the bending state display portion 17 is rotated in a same direction following clockwise or counterclockwise rotation of the bending wheel 41.

Therefore, the user can easily determine a bending angle (bending amount) of the second bending portion 2b2 by confirming a position of the rotation index 17m.

Figure 4C:
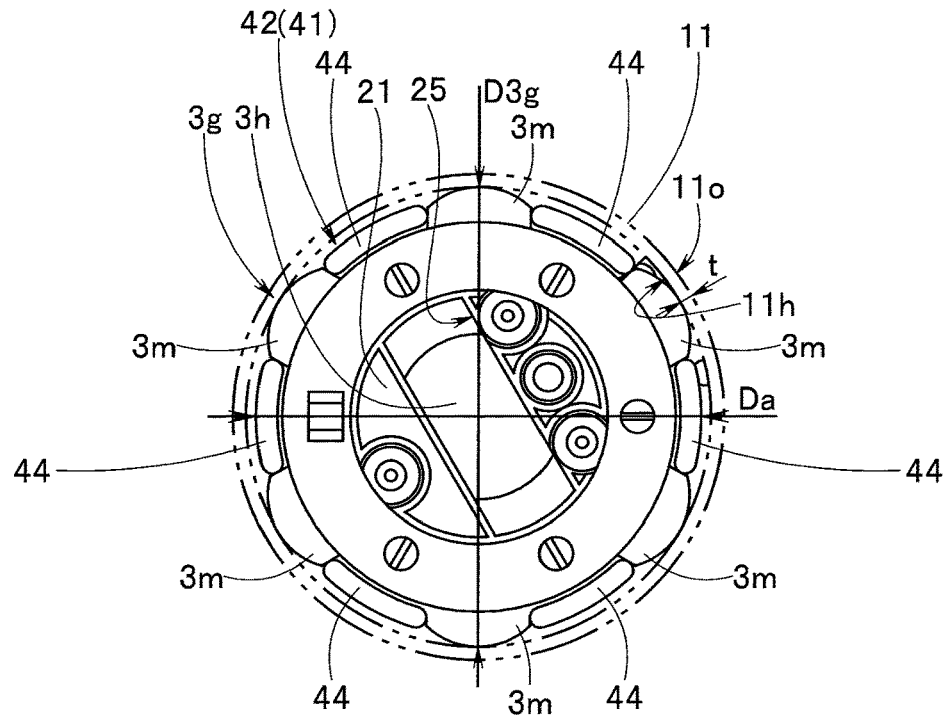
FIG. 4C is a view explaining an attached state in which a protruded portion of a knob connection portion is placed in a predetermined state in a recess of a second bending portion up-down operation knob.

In the present embodiment, as illustrated in FIG. 4C, an outside diameter Da of the knob connection portion 42 of the bending wheel 41 is set at a smaller diameter than an outside diameter D3g of the second UD knob 3g.

The knob outside diameter D3g of the second UD knob 3g is set to be smaller than an outer periphery outside diameter D3S in advance so as to be disposed inward from an outer peripheral surface (described as the outer periphery outside diameter D3S) of the sub operation portion 3S as illustrated in FIG. 2A.

Accordingly, in a state where the bending wheel 41 is integrated with the second UD knob 3g, an outer peripheral surface of the bending wheel 41 is located at a center side from an outer peripheral surface of the second UD knob 3g.

Reference sign 11h denotes an inner peripheral surface of a knob rotation portion housing hole portion of the housing case 11. An inside diameter of the inner peripheral surface 11h is set to be larger than the outside diameter D3g of the second UD knob 3g in advance.

In addition, a wall thickness t of the housing case 11 is set so that an outer peripheral surface 11o of the knob rotation portion housing hole portion 11h and the outer peripheral surface of the sub operation portion 3S are flush with each other in a placed state.

Note that the outer peripheral surface 11o of the knob rotation portion housing hole portion 11h may be set to be slightly larger than the outer peripheral surface of the sub operation portion 3S.

In this way, the outer peripheral surface of the bending wheel 41 is set to be disposed at the center side from the outer peripheral surface of the second UD knob 3g.

The wall thickness of the knob rotation portion housing hole portion 11h of the housing case 11 is properly set, and a diameter of the outer peripheral surface 11o of the knob rotation portion housing hole portion 11h is set to be equal to or slightly larger than a diameter of the outer peripheral surface of the sub operation portion 3S.

As a result, in a state where the outer shape of the housing case 11 is decreased and the housing case 11 is put on the second UD knob 3g to be placed on the sub operation portion 3S, it is possible to prevent the outer peripheral surface 11o of the knob rotation portion housing hole portion 11h of the housing case 11 from significantly protruding from the outer peripheral surface of the sub operation portion 3S and having an adverse effect on an operation of the first UD knob 3c, an operation of the first RL knob 3d, an operation of the first UD fixing lever 3e and the like.

The transmission portion 50 mainly includes a switching gear 51, a switching gear shaft 52, a cam ring 53, and a switching tab 16 that are illustrated in FIG. 4B.

Figure 4D:
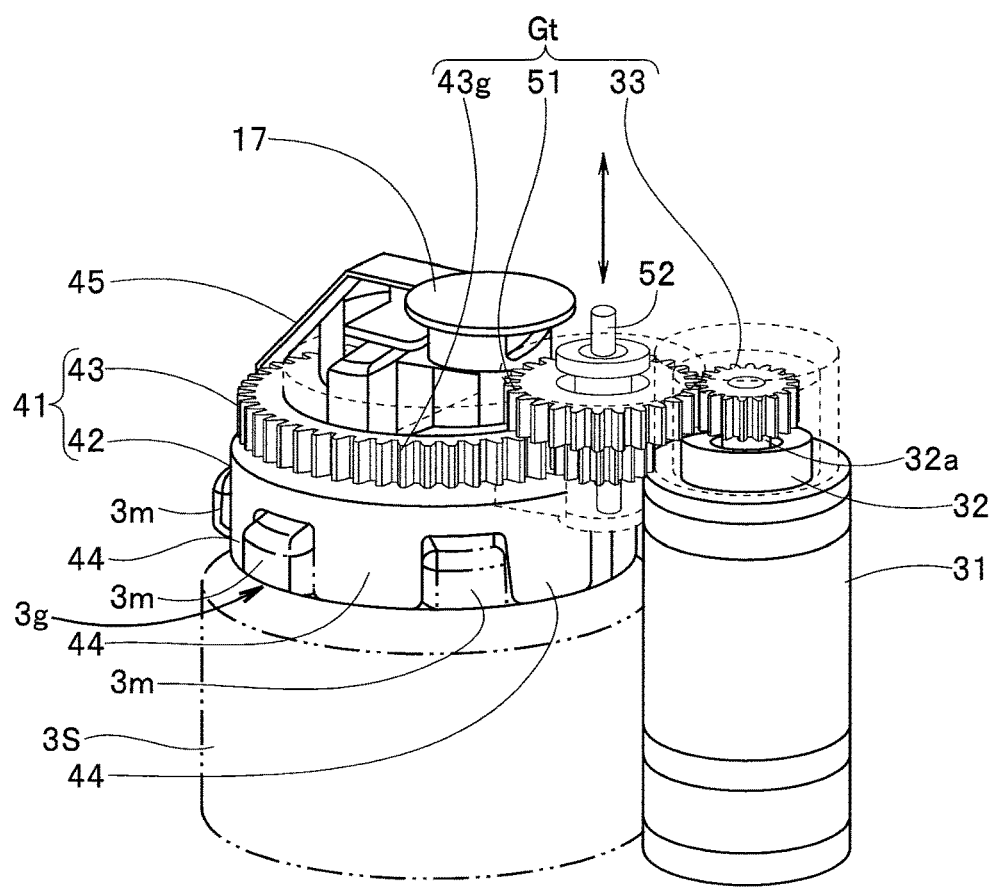
FIG. 4D is a view explaining a gear train configured by a switching gear and a gear of a meshing portion, and a driving gear fixedly provided on a motor shaft.

As described above, the switching gear 51 is fixedly provided at one end portion side of the switching gear shaft 52. The switching gear 51 configures a gear train Gt as illustrated in FIG. 4D, with the gear 43g of the meshing portion 43 of the aforementioned bending wheel 41, and the driving gear 33 fixedly provided on the motor shaft 32a.

As illustrated in FIG. 4B, at the other end portion of the switching gear shaft 52, an engaging protrusion 52a that protrudes in a direction orthogonal to the shaft 52 is provided.

A cam groove 53a for ring is formed in the cam ring 53. A protrusion 53b for ring protrudes from an outer peripheral surface of the cam ring 53.

The switching tab 16 includes a cylinder portion 16a, and a cam groove 16b for cylinder is formed in the cylinder portion 16a.

An outer peripheral surface side of the cam ring 53 is placed on an inner peripheral surface side of the cylinder portion 16a of the switching tab 16. In a state of the placement, the protrusion 53b for ring is disposed in the cam groove 16b for cylinder.

The engaging protrusion 52a is placed on an inner peripheral surface side of the cam ring 53. In a state of the placement, the engaging protrusion 52a is disposed in the cam groove 53a for ring.

According to the aforementioned configuration, the protrusion 53b for ring in the cam groove 16b for cylinder is moved with rotation of the switching tab 16, and the cam ring 53 is moved in an axial direction of the switching gear shaft 52.

In addition, with movement in the axial direction of the cam ring 53, the engaging protrusion 52a in the cam groove 53a for ring is moved in the axial direction.

As a result of the above, the switching gear 51 of the gear train Gt is moved in the axial direction of the switching gear shaft 52 with a switching operation to clockwise or counterclockwise of the switching tab 16 as illustrated in FIG. 4D.

As a result, the gear train Gt is switched to a state where the switching gear 51, the gear 43c of the meshing portion 43, and the driving gear 33 are meshed with one another, or a state where the switching gear 51, the gear 43c of the meshing portion 43 and the driving gear 33 are cut off from one another.

In a transmission state where the switching gear 51, the gear 43g of the meshing portion 43 and the driving gear 33 are meshed with one another, a rotational driving force of the motor 32 is transmitted to the bending wheel 41 and the second UD knob 3g is rotated.

In other words, the driving force of the motor 32 is not transmitted to the bending wheel 41 by bringing the switching gear 51, the gear 43c of the meshing portion 43, and the driving gear 33 into a cutoff state.

Figure 5A:
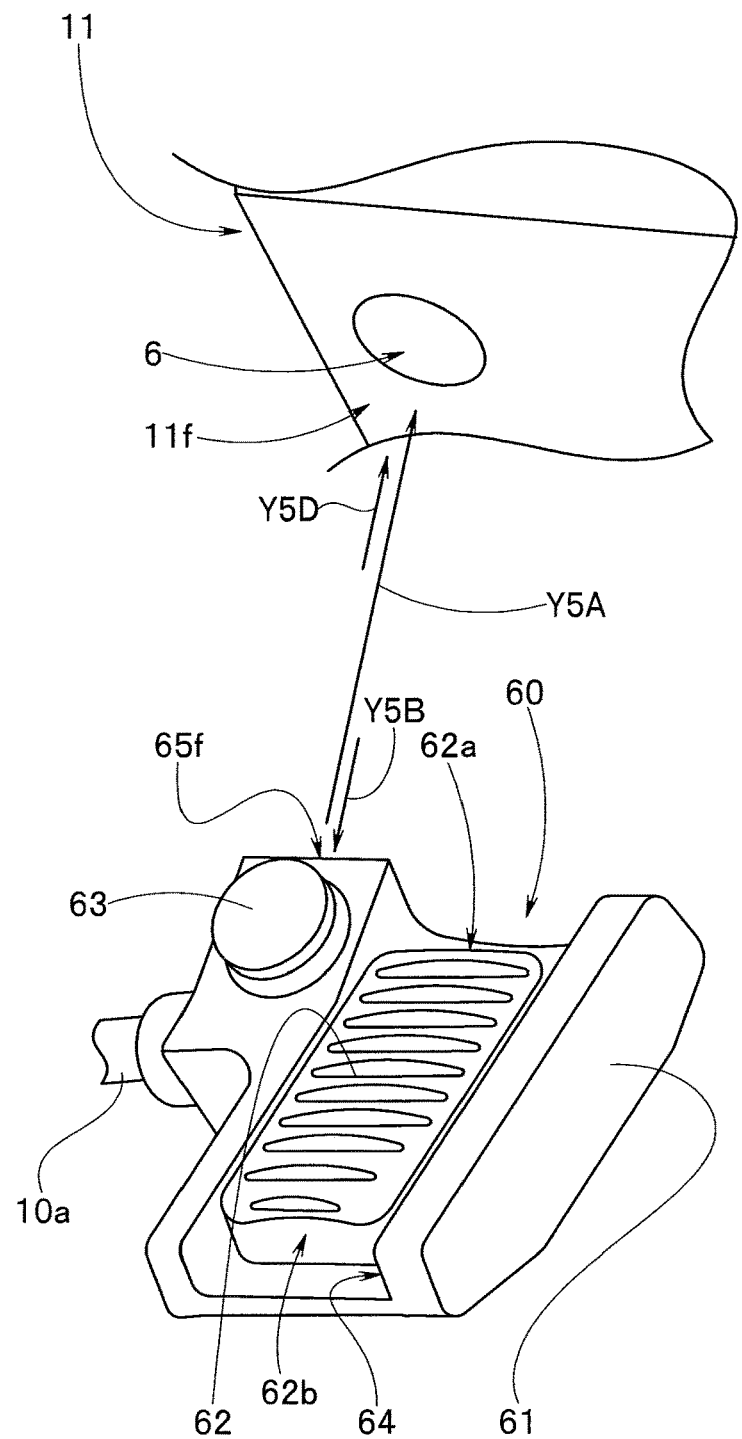
FIG. 5A is a view explaining a relationship between an operation switch that is attachable and detachable, and the housing case.

As illustrated in FIG. 5A, the operation switch 60 is fitted to an outer portion of the housing case 11 attachably and detachably as shown by an arrow Y5A.

The operation switch 60 has a case attaching portion (refer to reference sign 65 in FIG. 5B) on a switch side fitting surface 65f, and has an operation switch fixing portion 6 on a case side fitting surface 11f that is one surface configuring the outer portion of the housing case 11.

Figure 5B:
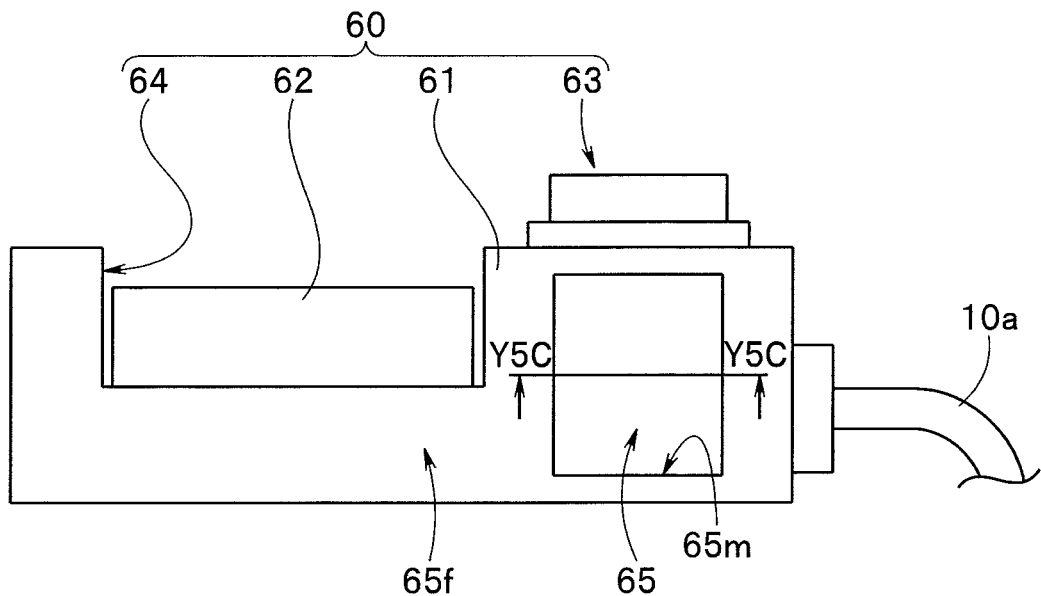
FIG. 5B is a view of the operation switch seen in an arrow 5B direction in FIG. 5A.

As illustrated in FIG. 5A and FIG. 5B, an operation element housing portion 64, and a case attaching portion are provided in the switch case 61 of the operation switch 60. The operation element housing portion 64 is a groove elongated in a longitudinal direction, and the operation element 62 is disposed slidably in the longitudinal direction.

The switch side fitting surface 65f and the case side fitting surface 11f are flat surfaces. The switch side fitting surface 65f and the case side fitting surface 11f are contact surfaces that contact each other in a fitted state.

Figure 5C:
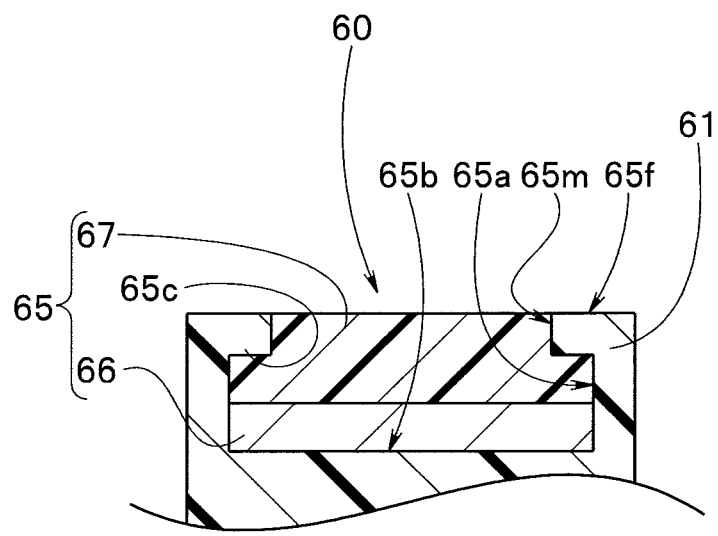
FIG. 5C is a sectional view along an arrows Y5C to Y5C line of a case attaching portion illustrated in FIG. 5B.

As illustrated in FIG. 5B, the case attaching portion 65 is provided at a predetermined position of the switch side fitting surface 65f. As illustrated in FIG. 5C, the case attaching portion 65 includes a soft magnetic body 66, and a sealing resin 67. Reference sign 65a denotes a hole for attaching portion.

The soft magnetic body 66 is a plate member that is formed of a soft magnetic material such as a carbon steel, and a ferrite stainless steel, and has a rectangular sectional shape, for example. The soft magnetic body 66 is disposed on a bottom surface 65b of the hole 65a for attaching portion.

The sealing resin 67 is an epoxy resin, for example. The sealing resin 67 prevents the soft magnetic body 66 from rusting. The sealing resin 67 is filled in the hole 65a for attaching portion after the soft magnetic body 66 is disposed in the hole 65a for attaching portion.

The sealing resin 67 that is filled seals the soft magnetic body 66. A surface on a rectangular opening 65m side of the sealing resin 67 after hardening is formed so as not to protrude from the switch side fitting surface 65f.

Note that the surface on the rectangular opening 65m side may be a same flat surface as the switch side fitting surface 65f. A rectangular opening 65m is an inner peripheral surface of an inner flange portion 65c.

Figure 5D:
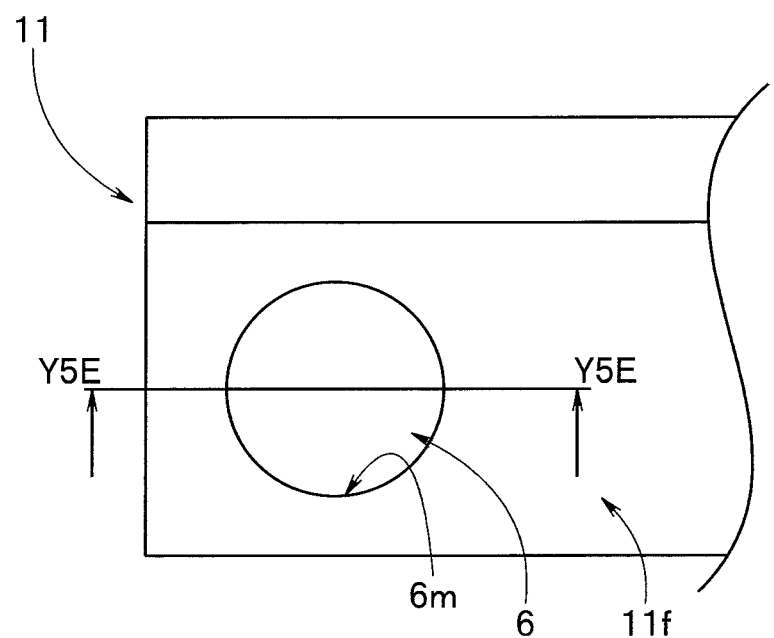
FIG. 5D is a view of the housing case seen in an arrow 5D direction in FIG. 5A.
Figure 5E:
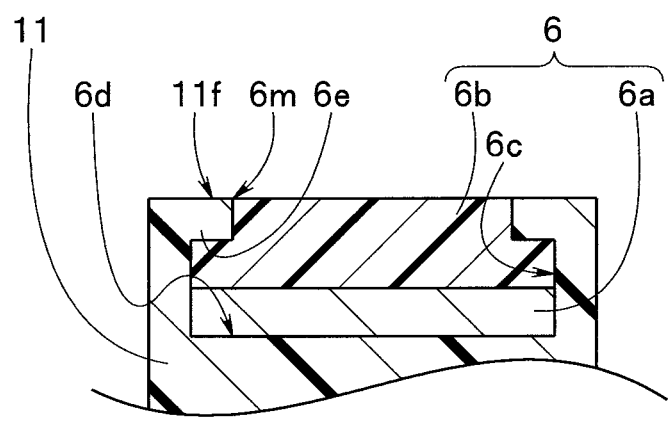
FIG. 5E is a sectional view along an arrows Y5E to Y5E line of an operation switch fixing portion illustrated in FIG. 5D.

As illustrated in FIG. 5D, the operation switch fixing portion 6 is provided at a predetermined position of the case side fitting surface 11f. As illustrated in FIG. 5E, the operation switch fixing portion 6 includes a permanent magnet 6a, and a sealing resin 6b. Reference sign 6c denotes a hole for fixing portion.

The permanent magnet 6a is a plate member circular in sectional shape, for example, and is disposed on a bottom surface 6d of the hole 6c for fixing portion.

The sealing resin 6b is, for example, an epoxy resin. The sealing resin 6b prevents the permanent magnet 6a from rusting. The sealing resin 6b is filled in the hole 6c for fixing portion after the permanent magnet 6a is disposed in the hole 6c for fixing portion.

The sealing resin 6b that is filled seals the permanent magnet 6a. A surface on the circular opening 6m side, of the sealing resin 6b after hardening is formed so as not to protrude from the case side fitting surface 11f.

Note that the surface on the circular opening 6m side may be a same flat surface as the case side fitting surface 11f. A circular opening 6m is an inner peripheral surface of an inner flange portion 6e.

The operation element 62 illustrated in FIG. 5A functions as a so-called slide switch.

Figure 6A:
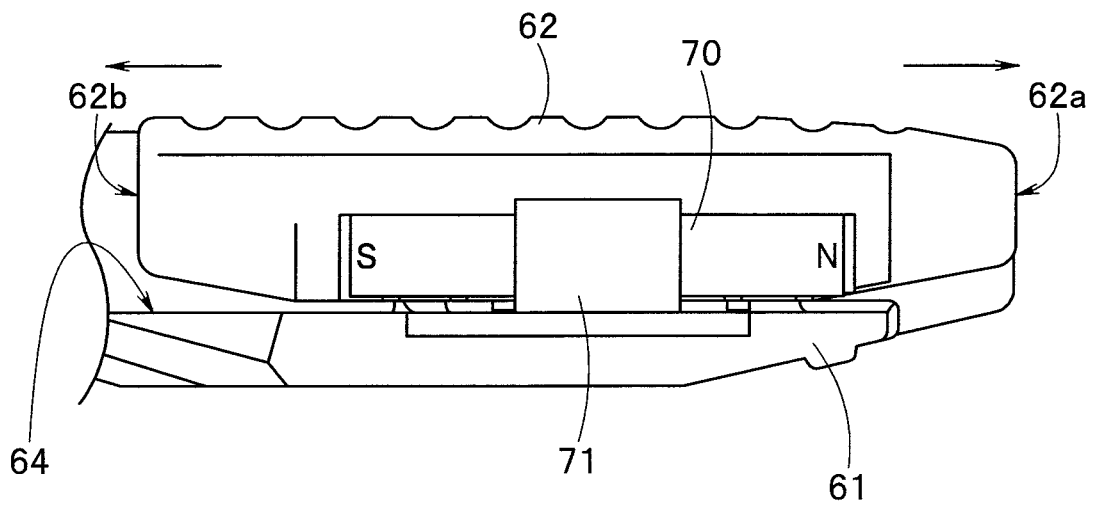
FIG. 6A is a view explaining a configuration example in which an operation element is a slide switch.

As illustrated in FIG. 6A, a magnet 70 is placed at a predetermined position of the operation element 62. In the case housing portion 64, a Hall sensor (hereinafter, abbreviated as a sensor) 71 configured to detect a magnetic field of the magnet 70 is provided at a predetermined position.

The sensor 71 outputs a predetermined driving control signal to a motor according to change in distances of a north pole and a south pole of the magnet 70.

More specifically, when a lower end 62b of the operation element 62 illustrated in FIG. 5A and FIG. 6A is located at a lowermost portion in a sliding range of the operation element housing portion 64, the sensor 71 outputs a first driving control signal to the motor 32.

As a result, the motor 32 is rotationally driven at a high speed to rotate the second UD knob 3g in a counterclockwise direction, for example.

In contrast with this, when an upper end 62a of the operation element 62 is located at an uppermost portion in the sliding range, the sensor 71 outputs a third driving control signal to the motor 32.

As a result, the motor 32 is rotationally driven at a high speed to rotate the second UD knob 3g in a clockwise direction, for example.

When the upper end 62a of the operation element 62 separates from a middle portion between the uppermost portion and the lowermost portion to an upper portion side by a predetermined distance, the sensor 71 outputs a fourth driving control signal to the motor 32.

Thereupon, the motor 32 is rotationally driven at a low speed to rotate the second UD knob 3g in the clockwise direction, for example.

In contrast with this, when the lower end 62b of the operation element 62 separates from the middle portion to a lower portion side by a predetermined distance, the sensor 71 outputs a second driving control signal to the motor 32.

Thereupon, the motor 32 is rotationally driven at a low speed to rotate the second UD knob 3g in the counterclockwise direction, for example.

Figure 6B:
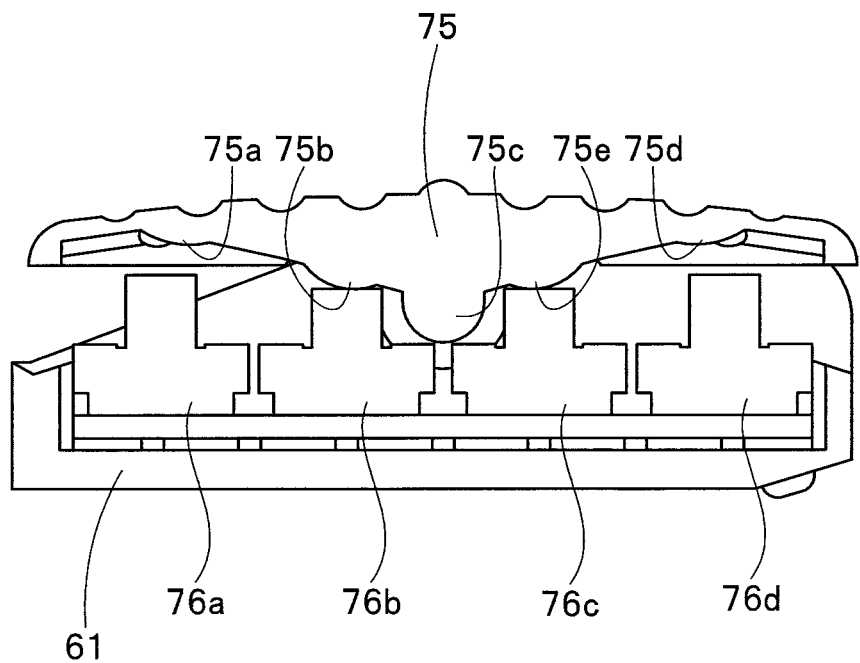
FIG. 6B is a view explaining a configuration example in which the operation element is a seesaw switch.

Note that in the aforementioned embodiment, the operation element 62 is a slide switch. However, the operation element may be a seesaw switch 75 that rotates clockwise or counterclockwise with a central protruded portion 75c as a fulcrum as illustrated in FIG. 6B.

In the seesaw switch 75, four switch protruded portions 75a, 75b, 75d, and 75e are provided. In the case housing portion 64, a plurality of, for example, four tactile switches 76a, 76b, 76c, and 76d are provided.

When the seesaw switch 75 is in an initial state, the second tactile switch 76b, and the third tactile switch 76c are in an on state, and the first tactile switch 76a, and the fourth tactile switch 76d are in an off state. At this time, the motor 32 is in a stopping state.

Figure 6C:
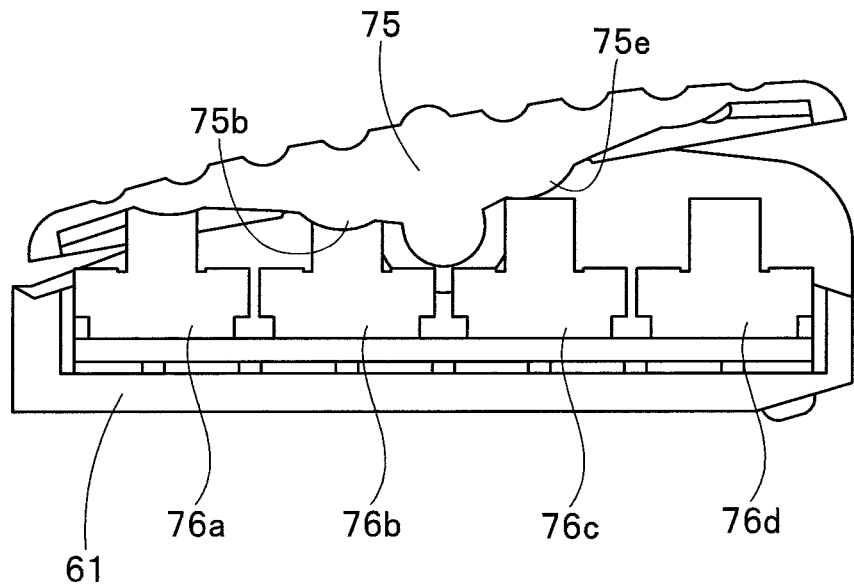
FIG. 6C is a view explaining an operation example of the seesaw switch.

When the seesaw switch 75 is rotated counterclockwise, the third tactile switch 76c is switched from the on state to an off state, and only the second tactile switch 76b is in the on state as illustrated in FIG. 6C, a second driving control signal is outputted to the motor 32. The motor 32 is driven at a low speed to rotate the second UD knob 3g in the counterclockwise direction.

Figure 6D:
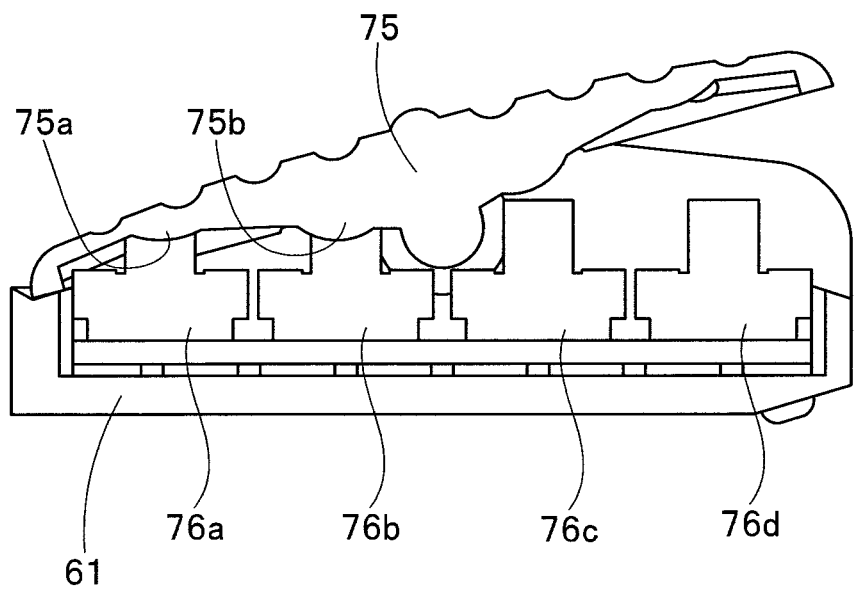
FIG. 6D is a view explaining another operation example of the seesaw switch.

Subsequently, the seesaw switch 75 is further rotated counterclockwise as illustrated in FIG. 6D, and thereby the first tactile switch 76a is brought into an on state in addition to the second tactile switch 76b.

Then, the first driving control signal is outputted to the motor 32. Thereupon, the motor 32 is driven at a high speed to rotate the second UD knob 3g in the counterclockwise direction.

Note that though not illustrated, when the motor 32 is in the stopping state, and the seesaw switch 75 is rotated clockwise, the second tactile switch 76b is switched from the on state to the off state, only the third tactile switch 76c is in the on state, and the fourth driving control signal is outputted to the motor 32.

Then, the motor 32 is driven at a low speed to rotate the second UD knob 3g clockwise.

Thereafter, the seesaw switch 75 is further rotated clockwise, and thereby the fourth tactile switch 76d is brought into the on state in addition to the third tactile switch 76c.

Then, the third driving control signal is outputted to the motor 32. Thereupon, the motor 32 is driven at a high speed to rotate the second UD knob 3g in the clockwise direction.

In this way, the operation element 62 provided in the operation switch 60 is operated to slide, or operated to rotate, whereby the driving control signal is outputted to the motor 32, and the second UD knob 3g is rotationally controlled by the driving force of the motor 32.

As a result, the user can cause the second bending portion 2b2 to perform bending operation without applying a large load to fingers.

Note that in the aforementioned embodiment, there are two speed levels, a high speed and a low speed.

However, driving control of the motor 32 may be performed to change the speed to one level or three levels or more, or stepwise based on the detection result of the Hall sensor 71.

The speed may be changed to the one level or the three levels or more by increasing or decreasing a number of tactile switches and a number of switch protruded portions.

Figure 7A:
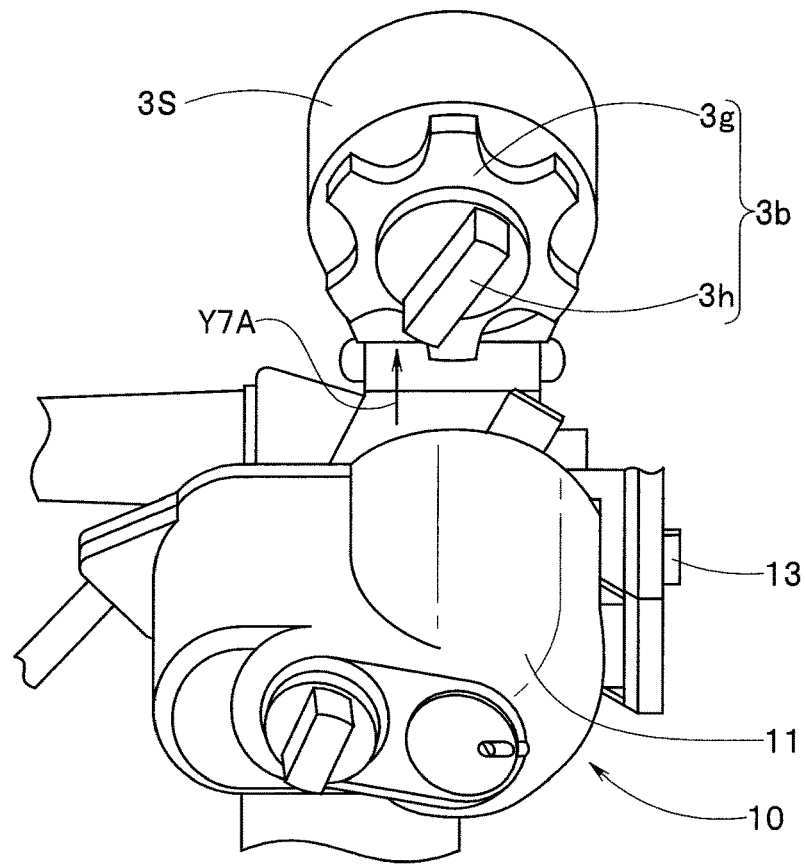
FIG. 7A is a view explaining a state where the housing case of the external mechanism for endoscope is attached to the sub operation portion.
Figure 7B:
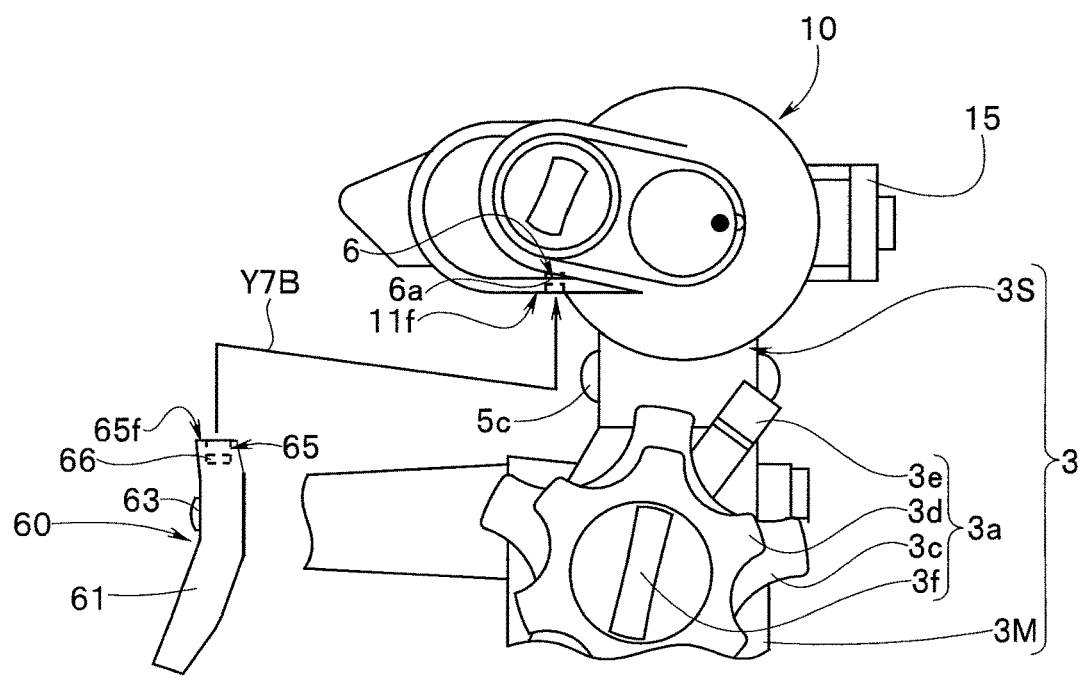
FIG. 7B is a view explaining attachment of the operation switch to the housing case attached to the sub operation portion.
Figure 7C:
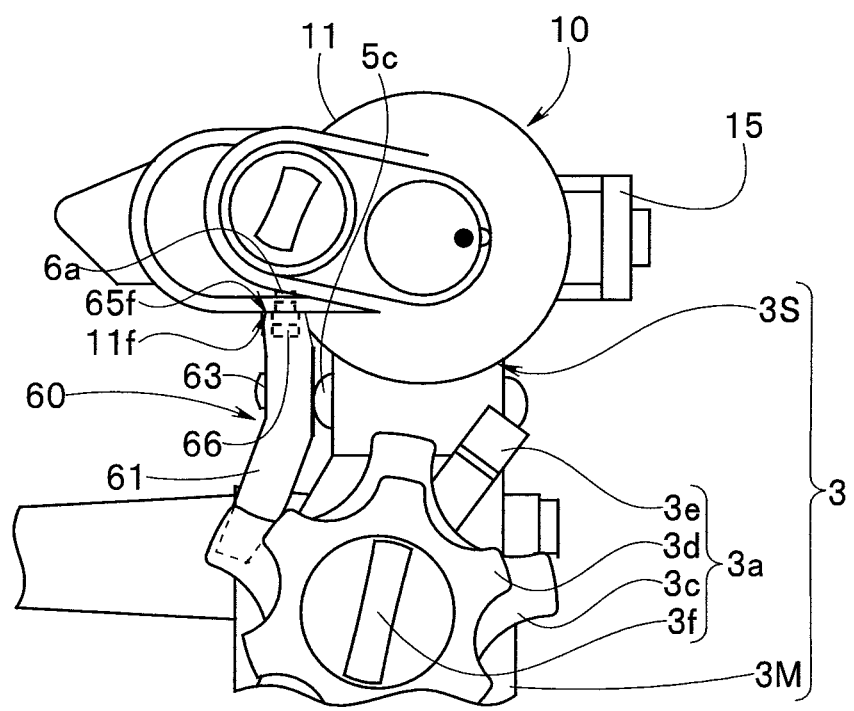
FIG. 7C is a view explaining a mechanism fitted state where the operation switch of the external mechanism for endoscope is placed adjacently to a first bending operation apparatus provided at a main operation portion.

With reference to FIG. 7A to FIG. 7C, attaching of the external mechanism 10 for endoscope to the sub operation portion 3S will be described.

First, in attaching the housing case 11 of the external mechanism 10 for endoscope to the sub operation portion 3S, the user prepares the operation switch 60.

The user confirms whether or not the second UD fixing tab 3h provided at the second UD knob 3g is in a free position in advance.

The user confirms that the second UD fixing tab 3h is disposed in the free position, and thereafter, causes the housing case 11 of the external mechanism 10 for endoscope to face the second UD knob 3g provided at the sub operation portion 3S as illustrated in FIG. 7A.

At this time, the user causes the bending wheel 41 of the knob rotation portion 40 placed in the case internal space to face the second UD knob 3g.

Next, the user brings the housing case 11 close to the second UD knob 3g as illustrated by an arrow Y7A in FIG. 7A.

The user causes the recess 25 for tab provided at the rotation mechanism portion main body 21 to face the second UD fixing tab 3h, and houses the second UD fixing tab 3h in the recess 25 for tab as illustrated in FIG. 4C described above.

As a result, the housing case 11 is disposed on the second UD knob 3g as illustrated in FIG. 2B described above.

In the housed and disposed state, the protruded portions 44 of the knob connection portion 42 are placed in the recesses of the second UD knob 3g, in the predetermined state, as illustrated in FIG. 4C described above, the second UD knob 3g and the bending wheel 41 are integrated, and attachment of the housing case 11 to the sub operation portion 3S is completed as illustrated in FIG. 7B.

Thereafter, the user moves the switch side fitting surface 65f toward the case side fitting surface 11f as shown by an arrow Y7B in FIG. 7B. The switch side fitting surface 65f includes the case attaching portion 65 of the operation switch 60. The case side fitting surface 11f includes the operation switch attaching portion 6 of the housing case 11.

Subsequently, the switch side fitting surface 65f is disposed on the case side fitting surface 11f as illustrated in FIG. 7C. Thereby, the permanent magnet 6a attracts the magnetic body 66 and fitting of the operation switch 60 to the housing case 11 is completed.

As a result, the housing case 11 to which the operation switch 60 is fitted is attached to the sub operation portion 3S, and attachment of the external mechanism 10 for endoscope to the sub operation portion 3S is completed.

Note that as illustrated in FIG. 7B, in the state where the housing case 11 is attached to the sub operation portion 3S, a remote switch 5c is exposed.

Thereafter, by completing fitting of the operation switch 60 to the housing case 11 as illustrated in FIG. 7C, the operation switch 60 is placed at a predetermined position adjacent to the first bending operation apparatus 3a provided in the main operation portion 3M.

As a result, the exposed remote switch 5c is brought into a state where the remote switch 5c is covered with the switch case 61. At this time, a remote switch side of the dummy switch 63 is disposed on the remote switch 5c.

In this state, the remote switch 5c is operable by pressing and operating the dummy switch 63 so that the dummy switch 63 moves in a thickness direction of the switch case 61.

Here, an operation of the endoscope 1 will be described, in which the external mechanism 10 for endoscope is attached to the sub operation portion 3S, and the operation switch 60 is placed adjacently to the first bending operation apparatus 3a.

The user grasps the main operation portion 3M when the user performs endoscopy with the endoscope 1 in which the external mechanism 10 for endoscope is attached to the sub operation portion 3S. Subsequently, the user grasps the insertion portion 2 with a different hand from the hand grasping the main operation portion 3M, and inserts the insertion portion 2 into a body via an oral cavity, for example.

At this time, the user properly causes the first bending portion 2b1 and the second bending portion 2b2 to perform a bending operation. In other words, the user properly performs a rotational operation of the first UD knob 3c or the first RL knob 3d of the first bending operation apparatus 3a provided at the main operation portion 3M to cause the first bending portion 2b1 to perform a bending operation in the up-down direction, in the left-right direction, or the like, whereas the user properly operates the operation element 62 of the operation switch 60 provided adjacently to the first bending operation apparatus 3a of the main operation portion 3M to cause the second bending portion 2b2 to perform a bending operation in the up-down direction.

In this way, by providing the operation switch 60 adjacently to the first bending operation apparatus 3a of the main operation portion 3M, the user can smoothly perform the rotational operation of the first UD knob 3c and the first RL knob 3d of the first bending operation apparatus 3a, the slide operation of the operation element 62 of the operation switch 60 and the like with fingers of the user that grasp the main operation portion 3M.

The user properly causes the first bending portion 2b1 and the second bending portion 2b2 that are provided at the bending portion 2b to perform bending operation by only moving the fingers slightly without touching the remote switch, and can perform insertion of the insertion portion 2 into a deep part in a body more smoothly.

After end of endoscopy, the endoscope 1 and the external mechanism 10 for endoscope are cleaned. As for the external mechanism 10 for endoscope of the present embodiment, the operation switch 60 is detached from the case side fitting surface 11f of the housing case 11, at a time of cleaning. Thereafter, the operation switch 60 that is a separate body, and the housing case 11 are respectively cleaned.

As above, the switch side fitting surface 65f of the operation switch 60 and the case side fitting surface 11f of the housing case 11 are made flat surfaces, and thereby a recess in which dust easily accumulates is eliminated from the fitting portion.

As a result, it is possible to improve cleanability of the external mechanism 10 for endoscope by reliably cleaning the operation switch 60 and the housing case 11 respectively.

It is possible to intensively clean the operation switch 60 alone that is detached from the housing case 11.

Note that in the aforementioned embodiment, the soft magnetic body 66 is provided in the case attaching portion 65 of the operation switch 60, and the permanent magnet 6a is provided in the operation switch fixing portion 6 of the housing case 11.

Regardless of the above, a permanent magnet may be provided in the case attaching portion 65 of the operation switch 60, and a soft magnetic body may be provided in the operation switch fixing portion 6 of the housing case 11.

The detached operation switch 60 may be discarded, and only the housing case 11 may be cleaned. This makes cleaning of the operation switch 60 unnecessary and can realize further improvement in cleanability.

In the aforementioned configuration, the soft magnetic body 66 is provided in the case attaching portion 65 of the operation switch 60 without a permanent magnet being provided.

As a result, in a state where a plurality of operation switches 60 for replacement are collectively housed in one storage box, for example, it is possible to take out the operation switches 60 in the storage box one by one.

In other words, a trouble that the case attaching portions 65 are attracted to one another to form a lump is prevented by providing the soft magnetic body 66 in each of the case attaching portions 65.

In the aforementioned embodiment, the switch side fitting surface 65f including the case attaching portion 65 is brought into contact with the case side fitting surface 11f including the operation switch attaching portion 6 of the housing case 11. Thereby, the operation switch 60 attracts the magnetic body with the permanent magnet and is integrally fixed to the housing case 11.

Figure 8A:
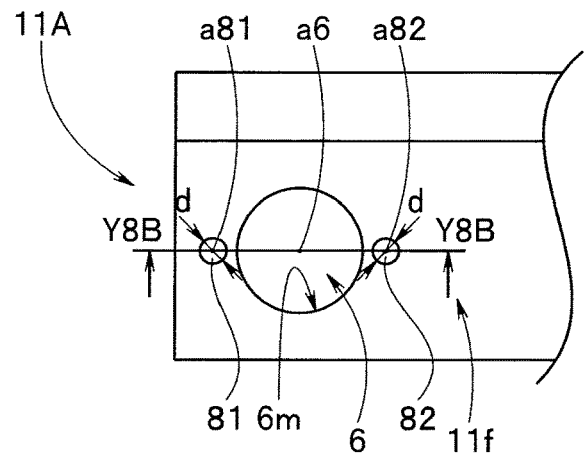
FIG. 8A is a view explaining an operation switch fixing portion provided with a column protrusion, that is an embodiment in which a part of a case attaching portion and a part of the operation switch fixing portion are modified.
Figure 8B:
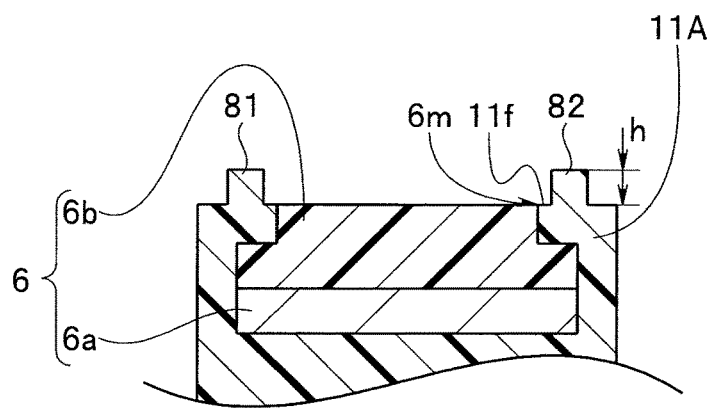
FIG. 8B is a sectional view along an arrows Y8B to Y8b line of the operation switch fixing portion illustrated in FIG. 8A.
Figure 8C:
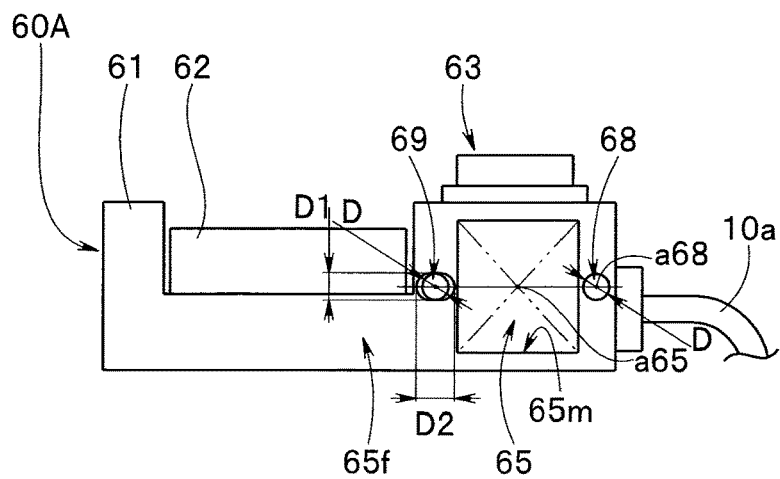
FIG. 8C is a view explaining the case attaching portion provided with a positioning hole in which the column protrusion is fitted, and a long slot in which the column protrusion is smoothly inserted.

In this mode, as illustrated in FIG. 8A to FIG. 8C, a pair of, for example, column protrusions 81 and 82 are provided as protrusions on the case side fitting surface 11*f* of the housing case 11A, while a positioning hole 68 and a long slot 69 are provided as recesses on the switch side fitting surface 65*f* of the operation switch 60A.

As illustrated in FIG. 8A and FIG. 8B, the column protrusions 81 and 82 protrude from the case side fitting surface 11*f* in a vicinity of an operation switch fixing portion 6.

In the pair of column protrusions 81 and 82, a protruding amount is denoted by h, and a diameter is denoted by d. The first column protrusion 81 and the second column protrusion 82 are provided in a predetermined positional relationship with a center axis a6 of a circular opening 6*m* between the first column protrusion 81 and the second column protrusion 82.

In the present embodiment, the center axis a6 is located on a line connecting a center axis a81 of the first column protrusion 81 and a center axis a82 of the second column protrusion 82.

As illustrated in FIG. 8C, the positioning hole 68 and the long slot 69 are provided in a predetermined positional relationship with a center axis a65 of a rectangular opening 65*m* between the positioning hole 68 and the long slot 69, in a vicinity of the case attaching portion 65 of the switch side fitting surface 65*f*. In the present embodiment, the center axis a65 and a center axis a68 of the positioning hole 68 are located on an extension line of the long slot 69.

The positioning hole 68 is a hole in which the first column protrusion 81 is fitted. An inside diameter D of the positioning hole 68 is set in advance to be slightly larger than the diameter d of the first column protrusion 81, and a depth is set to be larger than the protruding amount h.

As a result, the first column protrusion 81 is fitted into the positioning hole 68 with a predetermined fit.

In contrast with this, the long slot 69 is a hole in which the second column protrusion 82 is smoothly inserted. A width of the long slot 69 is set at D1 that is slightly larger than the diameter d of the second column protrusion 82, and a depth is set similarly to the depth of the positioning hole 68. A length in an extension line direction of the long slot 69 is set at D2 that is larger than the width D1.

Accordingly, when the column protrusions 81 and 82 and the holes 68 and 69 are in an allowable range, the second column protrusion 82 is smoothly inserted into the long slot 69.

In the aforementioned configuration, when the operation switch 60A is fitted to the housing case 11A, the first column protrusion 81 is fitted into the positioning hole 68 while the second column protrusion 82 is inserted into the long slot 69 on the case attaching portion 65 side.

As a result, a permanent magnet attracts a magnetic body, and the operation switch 60A is integrally fixed to the housing case 11A.

In this way, the holes 68 and 69 are provided on an operation switch 60A side, and the protrusions 81 and 82 are provided on a housing case 11A side.

As a result, it is possible to realize best operability by reliably installing the operation switch 60A in the predetermined position with respect to the housing case 11A. The permanent magnet and the magnetic body face each other in a predetermined positional relationship and realize a best attraction state to be in a stable fixation state.

Note that when the positioning hole 68 and the long slot 69 are provided on the switch side fitting surface 65*f* of the operation switch 60A, the inside diameter D is set with a size of a cleaning tool taken into consideration.

This makes it possible to easily clean insides of the holes 68 and 69 when cleaning the operation switch 60A alone. The operation switch 60A after use may be discarded to give priority to cleanability.

It is also conceivable to provide the protrusions 81 and 82 instead of providing the holes 68 and 69 on the operation switch 60A side, and provide the holes 68 and 69 instead of providing the protrusions 81 and 82 on the housing case 11A side. However, when cleanability is considered, the protrusions are provided on the housing case 11A side.

In the aforementioned embodiment, the operation switches 60 and 60A and the housing cases 11 and 11A are fitted by attracting the magnetic bodies with the permanent magnets.

However, the operation switch and the housing case may be configured as illustrated in FIG. 9A to FIG. 9E, or as illustrated in FIG. 10A to FIG. 10E. Operation switches 60B and 60C shown below of these configurations are of a type that is discarded after use.

With reference to FIG. 9A to FIG. 9F, another configuration of the operation switch and the housing case will be described.

Figure 9A:
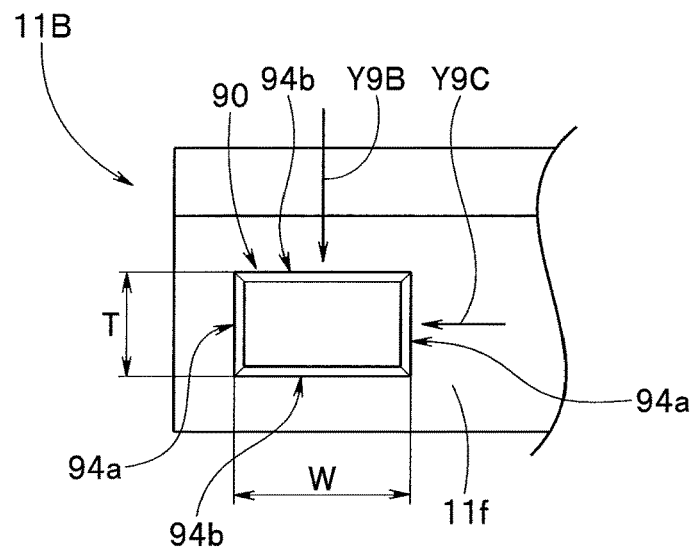
FIG. 9A is a view illustrating the housing case in which a fitting protrusion is provided on a case side fitting surface, according to another configuration example of the case attaching portion and the operation switch fixing portion.

As illustrated in FIG. 9A, on a case side fitting surface 11*f* of a housing case 11B, a square-shaped fitting protrusion 90 is provided as an operation switch fixing portion.

The fitting protrusion 90 protrudes by a predetermined amount from the case side fitting surface 11*f*, and a width of the protrusion 90 is denoted by W, and a thickness is denoted by T.

Figure 9B:
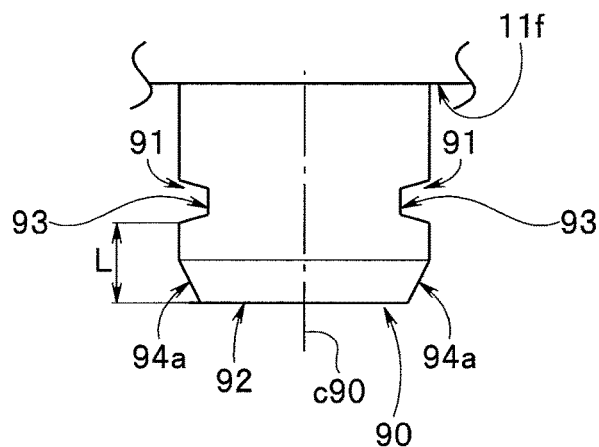
FIG. 9B is a view of the fitting protrusion seen in an arrow Y9B direction in FIG. 9A.
Figure 9C:
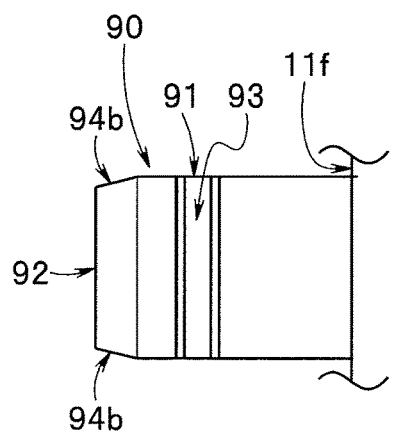
FIG. 9C is a view of the fitting protrusion seen in an arrow Y9C direction in FIG. 9A.

As illustrated in FIG. 9B and FIG. 9C, the fitting protrusion 90 includes a pair of fitting grooves 91 each in a predetermined shape, in a middle portion.

The fitting grooves 91 are provided in a symmetric positional relationship, with a protrusion center line c90 between the fitting grooves 91. The fitting grooves 91 each include a positioning surface 93 at a position separated from a protrusion end surface 92 by a predetermined distance. Reference signs 94*a* and 94*b* denote escape surfaces.

Figure 9D:
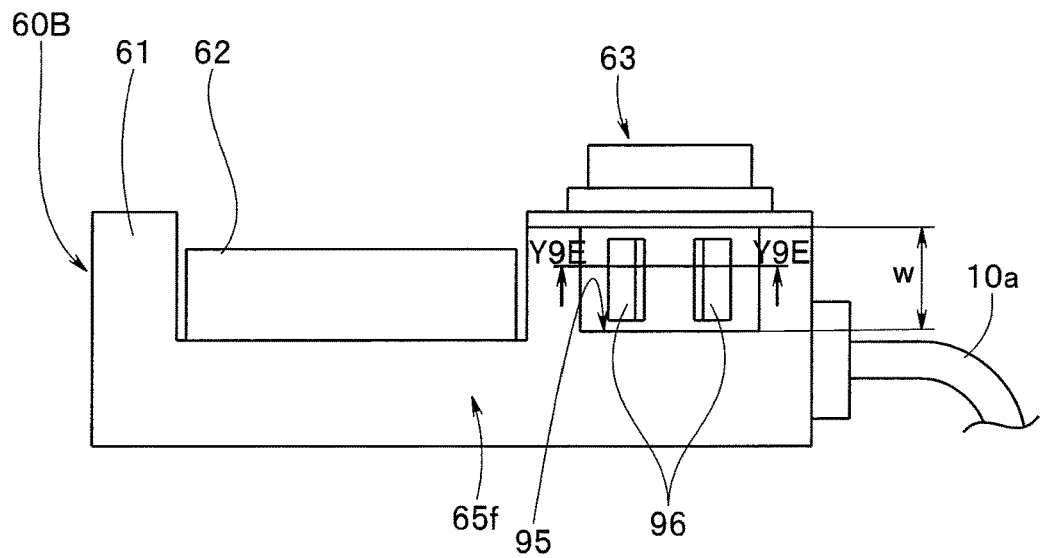
FIG. 9D is a view illustrating the operation switch in which a protrusion fitting hole is provided in a switch side fitting surface.

As illustrated in FIG. 9D, on a switch side fitting surface 65*f* of the operation switch 60B, a protrusion fitting recess (hereinafter, abbreviated as a fitting hole) 95 that is square-shaped in sectional shape is provided as a case attaching portion.

A pair of holding claws 96 are provided in the fitting hole 95. Reference sign w denotes an opening width. The opening width w is set to be slightly larger than the thickness T.

Figure 9E:
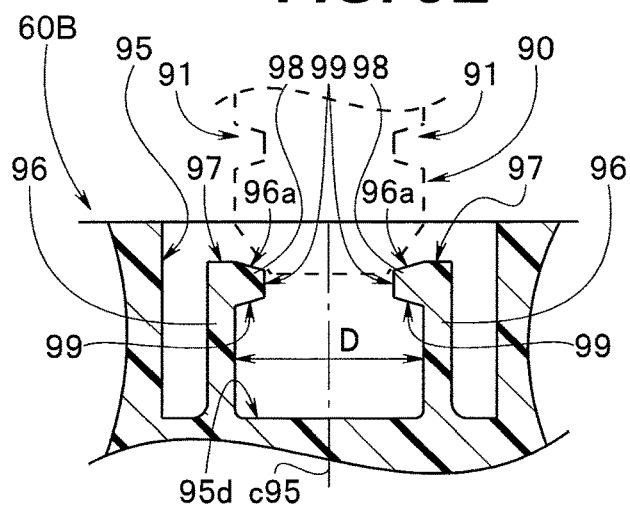
FIG. 9E is a view of the protrusion fitting hold seen in a direction of arrows Y9E to Y9E in FIG. 9D, and a view explaining a relationship between the fitting protrusion and the protrusion fitting hole.

As illustrated in FIG. 9E, the holding claws 96 face each other with a center line c95 between the holding claws 96. The holding claw 96 protrudes by a predetermined amount from a bottom surface 95*d* of the fitting hole 95, and is formed to be elastically deformed.

A space between the holding claws 96 is denoted by D, and is set to be slightly smaller than the width W. On an end surface 97 side of the holding claw 96, a protrusion 98 that protrudes to a center line c95 side is provided.

The protrusion 98 is disposed in a predetermined state inside the fitting groove 91. In the disposition state, an end surface 98*a* of the protrusion 98 abuts on a bottom surface 93*d* of the fitting groove 91, and an abutment surface 99 abuts on the positioning surface 93. Reference sign 96*a* denotes an escape surface.

Figure 9F:
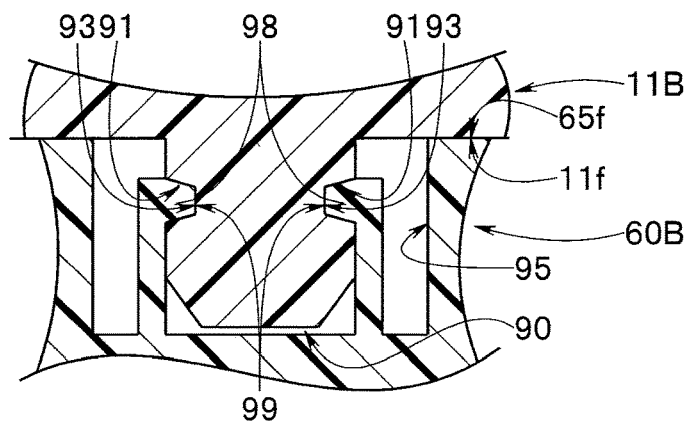
FIG. 9F is a view explaining a state where the fitting protrusion is disposed by being fitted in the protrusion fitting hole, and the operation switch and the housing case are integrally fixed.

Operations of the operation switch 60B and the housing case 11B will be described with reference to FIG. 9E and FIG. 9F.

In the aforementioned configuration, when the operation switch 60B is fitted to the housing case 11B, the fitting protrusion 90 of the housing case 11B is inserted into the fitting hole 95 of the operation switch 60B as shown by a broken line in FIG. 9E.

At this time, the escape surfaces 94b of the fitting protrusion 90 are firstly guided into the fitting hole 95, and thereafter, the escape surfaces 94a face the escape surfaces 96a in the fitting hole 95. Here, the operation switch 60B is further moved in a case side fitting surface 11f direction.

Then, the holding claws 96 are elastically deformed to enlarge the space D, and the protrusion end surface 92 passes between the protrusions 98. Subsequently, the holding claws 96 are restored to an original state as illustrated in FIG. 9F, the protrusions 98 are disposed in the fitting grooves 91, and the switch side fitting surface 65f closely contacts the case side fitting surface 11f.

At this time, the fitting protrusion 90 with the thickness T is fitted and disposed in the fitting hole 95 with the opening width w, and the protrusions 98 are disposed in the fitting grooves 91 by an elastic force of the holding claws 96, whereby the abutment surfaces 99 abut on the positioning surfaces 93. As a result, the operation switch 60B and the housing case 11B are integrally fixed.

In this way, the pair of holding claws 96 are provided in the fitting hole 95 provided in the operation switch 60B, and the fitting protrusion 90 that is disposed with one side fitted in the fitting hole 95 is provided on the housing case 11B side.

As a result, it is possible to realize best operability by reliably fixing the operation switch 60B and the housing case 11B in a predetermined position by making the permanent magnet and the magnetic body unnecessary.

Note that in the configuration in which the holding claws 96 are provided in the fitting hole 95 of the operation switch 60B, the operation switch 60B after use can be discarded.

It is also conceivable to provide the fitting protrusion 90 on the operation switch 60B side instead of providing the fitting hole 95, and provide the fitting hole 95 on the housing case 11B side instead of providing the fitting protrusion 90. However, when cleanability is taken into consideration, the fitting protrusion is provided on the housing case 11B side.

Next, another configuration of the operation switch and the housing case will be described with reference to FIG. 10A to FIG. 10E.

Figure 10A:
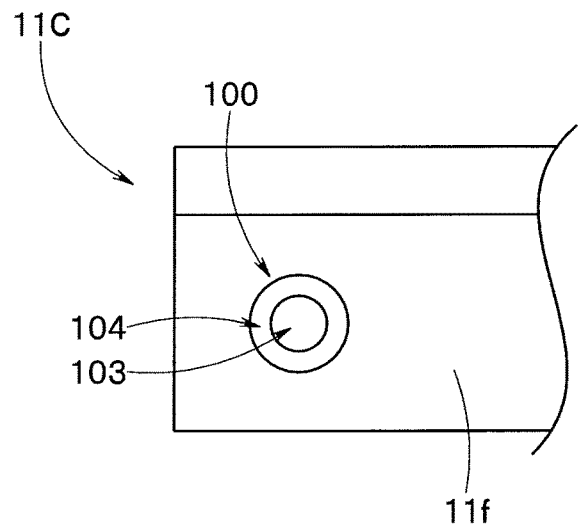
FIG. 10A is a view illustrating a housing case in which a column protruded portion is provided on a case side fitting surface, according to another configuration example of the case attaching portion and the operation switch fixing portion.
Figure 10B:
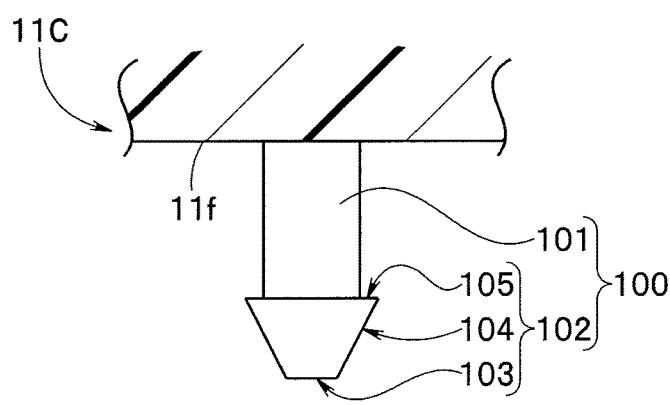
FIG. 10B is a view explaining the column protruded portion.

As illustrated in FIG. 10A and FIG. 10B, on a case side fitting surface 11f of a housing case 11C, a column protruded portion 100, for example, is provided as an operation switch fixing portion.

The column protruded portion 100 includes a column portion 101, and an engaging distal end portion 102. The engaging distal end portion 102 has a distal end plane 103, an inclined side surface 104, and an abutting proximal end surface 105. An outside diameter of the abutting proximal end surface 105 is larger than an outside diameter of the column portion 101. The inclined side surface 104 is a taper surface.

Figure 10C:
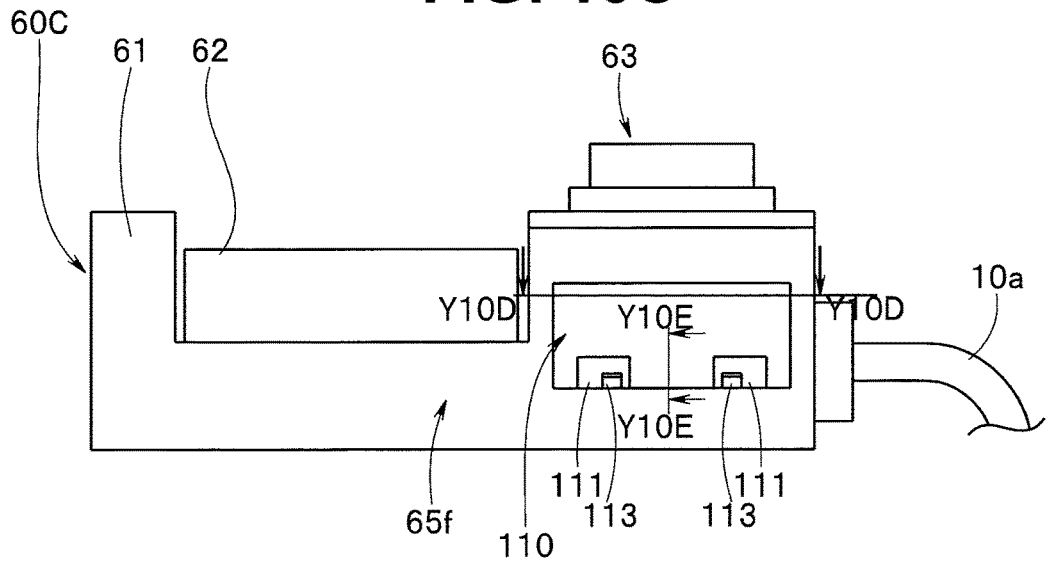
FIG. 10C is a view illustrating an operation switch in which a protrusion engaging hole is provided in a switch side fitting surface.
Figure 10D:
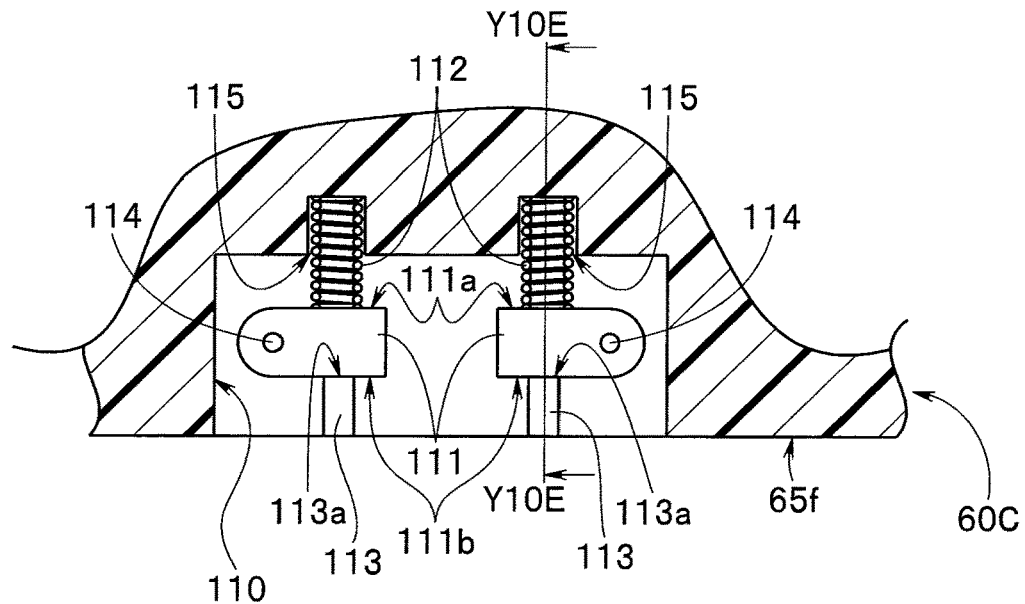
FIG. 10D is a view of the protrusion engaging hole seen in a direction of arrows Y10D to Y10D in FIG. 10C.

In contrast with this, as illustrated in FIG. 10C and FIG. 10D, on a switch side fitting surface 65f of an operation switch 60C, a protrusion locking hole (hereinafter, abbreviated as a locking hole) 110 that is square-shaped in opening shape is provided as a case attaching portion.

A pair of locking pieces 111, a pair of urging members 112, and a pair of holding portions 113 are provided in the locking hole 110. A space between the holding portions 113 is set to be larger than an outside diameter of the abutting proximal end surface 105. In contrast with this, a space between the locking pieces 111 is set to be smaller than the outside diameter of the abutting proximal end surface 105 by a predetermined dimension.

The locking pieces 111 are rotatably supported axially by rotation pins 114 fixedly provided on one surface of the locking hole 110 as illustrated in FIG. 10D.

Figure 10E:
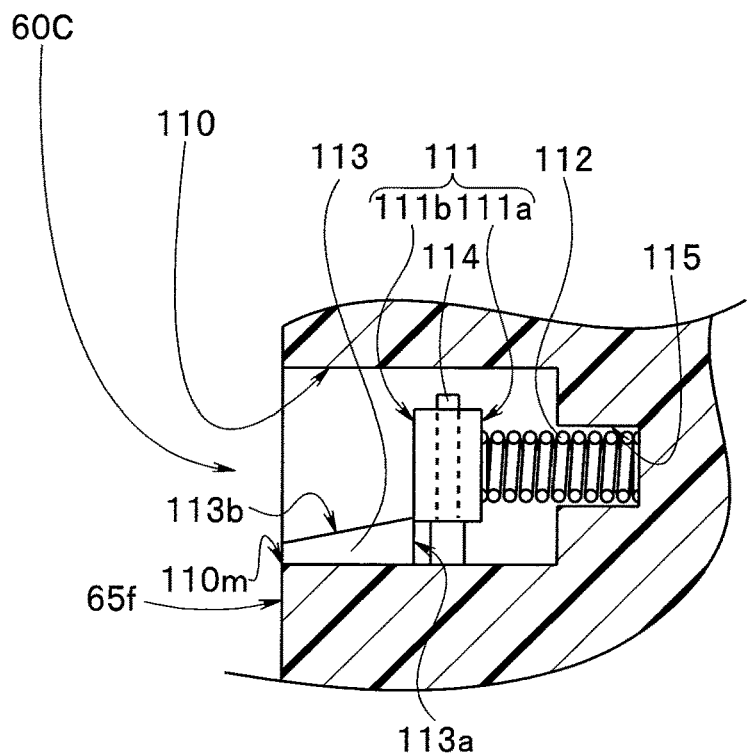
FIG. 10E is a sectional view along an arrows Y10E to Y10E line in FIG. 10D.

As illustrated in FIG. 10D and FIG. 10E, one end side of the urging member 112 is placed in a holding hole 115.

In the urging member 112, the other end located in the locking hole 110 abuts on and urges one side surface 111a of the locking piece 111. A part of the other side surface 111b of the locking piece 111 abuts on a holding surface 113a of the holding portion 113 and is prevented from rotating and is held.

Note that reference sign 113b denotes an inclined surface. The inclined surface 113b has a height set to be lower as it is closer to an opening 110m of the locking hole 110 from a holding surface 113a side.

Operations of the operation switch 60C and the housing case 11C will be described with reference to FIG. 10F to FIG. 10J.

Figure 10F:
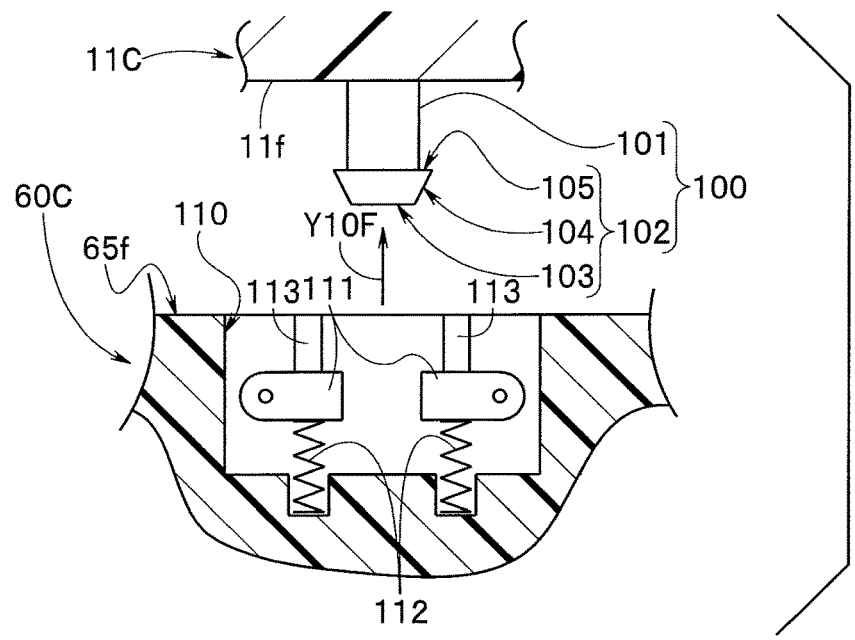
FIG. 10F to FIG. 10J are views explaining an operation of an operation switch and the housing case, and are views explaining a procedure to cause a locking hole of the operation switch to face a column protruded portion of the housing case, and cause the operation switch to move toward the housing case.

In the aforementioned configuration, when the operation switch 60C is fitted to the housing case 11C, the locking hole 110 of the operation switch 60C is caused to face the column protruded portion 100 of the housing case 11C as illustrated in FIG. 10F, and a gap between the locking pieces 111 is moved toward the engaging distal end portion 102 as shown by an arrow Y10F. Then, the inclined side surface 104 of the engaging distal end portion 102 abuts on the pair of locking pieces 111.

Figure 10G:
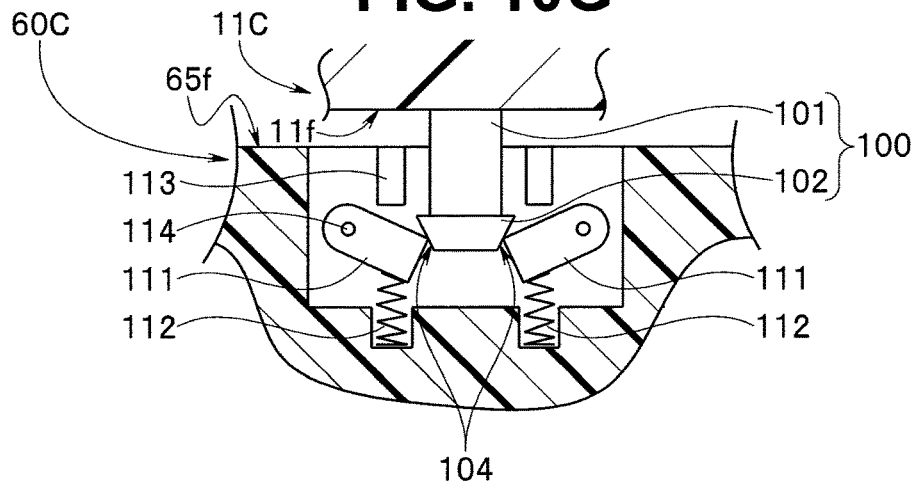

With further movement of the operation switch 60C thereafter, the locking pieces 111 are rotated around the rotation pins 114 against the urging forces of the urging members 112 as illustrated in FIG. 10G.

Figure 10H:
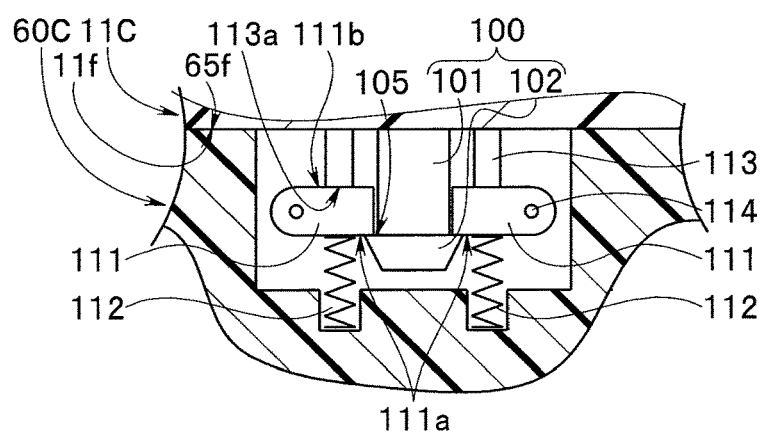

At a same time as the inclined side surface 104 of the engaging distal end portion 102 passes through the pair of locking pieces 111, the case fitting surface 11f and the switch side fitting surface 65f abut on each other as illustrated in FIG. 10H.

Then, the locking pieces 111 are rotated by the urging forces of the urging members 112, the other side surfaces 111b of the locking pieces 111 abut on the holding surfaces 113a of the holding portions 113, and the abutting proximal end surface 105 of the engaging distal end portion 102 abuts on the one side surfaces 111a of the locking pieces 111. As a result, the operation switch 60C and the housing case 11C are integrally fixed.

In this way, in the locking hole 110 provided in the operation switch 60C, the pair of locking pieces 111 that rotate with the rotation pins 114 as axes, the pair of urging members 112, and the pair of holding portions 113 are provided.

On the housing case 11C side, the column protruded portion 100 having the engaging distal end portion 102 is provided.

As a result, it is possible to realize best operability by reliably fixing the operation switch 60C and the housing case 11C in the predetermined position by making the permanent magnet and the magnetic body unnecessary similarly to the embodiment illustrated in FIG. 9A to FIG. 9F described above.

Figure 10I:
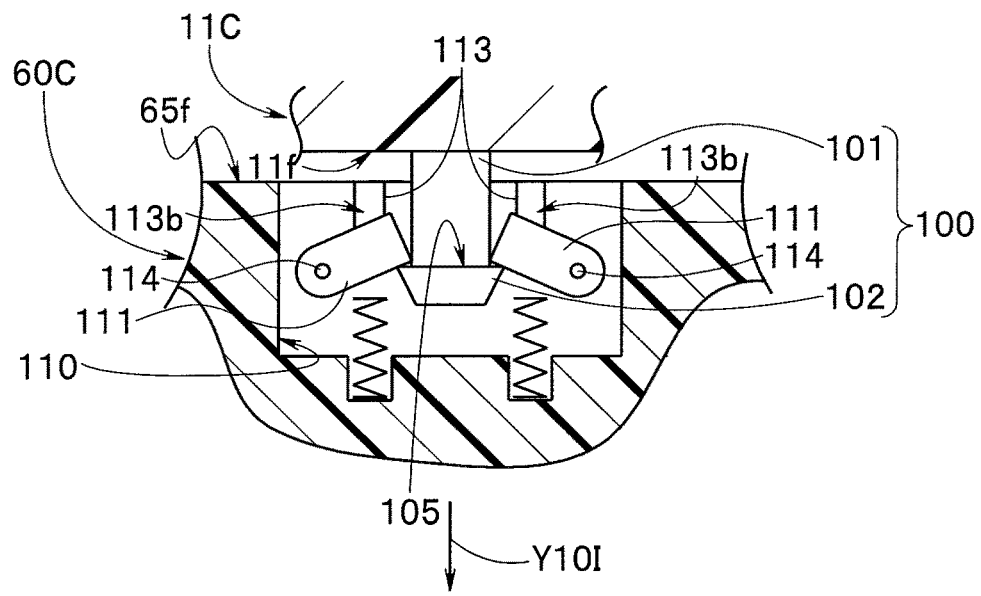
Figure 10J:
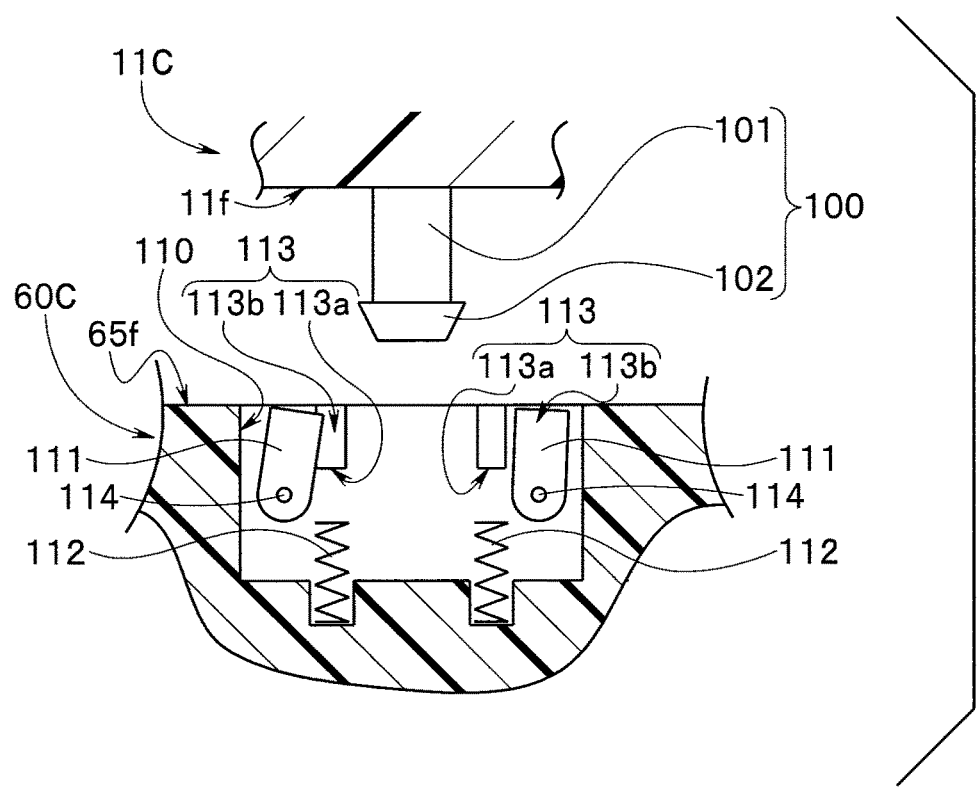

Note that in the present embodiment, after end of endoscopy, the operation switch 60C is moved with respect to the housing case 11C as shown by an arrow Y10I in FIG. 10I, and thereafter, the operation switch 60C is detached from the housing case 11C as illustrated in FIG. 10J.

The operation switch 60C is moved as illustrated in FIG. 10I from a state where the abutting proximal end surface 105 of the engaging distal end portion 102 abuts on the one side surfaces 111a of the locking pieces 111, and thereby an external force from the engaging distal end portion 102 works on the locking pieces 111.

Then, the locking pieces 111 that abut as illustrated in FIG. 10E ride over ridge lines configured by the holding surfaces 113a and the inclined surfaces 113b of the holding portions 113 and move onto the inclined surfaces 113b.

Thereafter, the column protruded portion 100 of the housing case 11C is pulled out of the locking hole 110 of the operation switch 60C.

Thereby, the locking pieces 111 move to inclined surface 113b sides as illustrated in FIG. 10J, for example, and cannot be restored to a state where the locking pieces 111 are urged by the urging members 112. In other words, the operation switch 60C is brought into a state where the operation switch 60C is hindered from reengagement and cannot be reused.

Accordingly, after end of the endoscopy, in the external mechanism 10 for endoscope of the present embodiment, only the housing case 11C is cleaned.

Note that in the aforementioned explanation, the external mechanism 10 for endoscope is fitted to the sub operation portion 3S, and the second bending portion 2b2 is caused to perform a bending operation without exerting a large load on fingers of the user.

However, the knob to which the external mechanism 10 for endoscope is fitted is not limited to the second UD knob 3g provided at the sub operation portion 3S, but may be the first RL knob 3d or both the first UD knob 3c and the first RL knob 3d, provided at the main operation portion 3M.

The present invention is not limited to the aforementioned embodiment, and can be properly changed within the range without departing from the gist or the idea of the invention read from the claims and the entire specification.

What is claimed is:

1. An external mechanism for use with an endoscope, the external mechanism comprising:
   one or more first protrusions configured to engage with one or more first recesses of an operation knob provided at an operation portion of the endoscope;
   an actuator configured to generate a driving force for rotating the one or more first protrusions;
   a housing case configured to house the one or more first protrusions and the actuator, and to be detachably attached to the operation portion; and
   an operation switch configured to be detachably fitted to an outer portion of the housing case, and to output a control signal to the actuator,
   wherein the housing case and the operation switch have respective first and second contact surfaces configured to contact each other in a fitting state where the operation switch is fitted to the housing case, and
   one of the first contact surface and the second contact surface having one or more second recesses and another of the first contact surface and the second contact surface having one or more second protrusions engaged with the one or more second recesses.

2. The external mechanism according to claim 1, wherein the first contact surface and the second contact surface are configured to attract each other by a magnetic force.

3. The external mechanism according to claim 1, wherein when an engagement state of the one or more second protrusions or the one or more second recesses provided on the first contact surface, and the one or more second protrusions or the one or more second recesses provided on the second contact surface being released, the one or more second protrusions or the one or more second recesses provided on at least one of the first and second contact surfaces being configured to deform such that re-engagement is hindered.

4. The external mechanism according to claim 1, wherein one of the one or more second protrusions and the one or more second recesses provided on the first contact surface or the one or more second protrusions and the one or more second recesses provided on the second contact surface being configured to elastically deform at an engaging operation time, and at a fitting time when the engaging operation is completed, elastic deformation is released, whereby the one or more second protrusions or the one or more second recesses provided on the first contact surface, and the one or more second protrusions or the one or more second recesses provided on the second contact surface being held in a fitting state.

5. The external mechanism according to claim 1, wherein the one or more second protrusions are provided on the first contact surface of the housing case, and the one or more second recesses being provided on the second contact surface of the operation switch.

6. An endoscope apparatus comprising:
   the external mechanism according to claim 1, and
   the endoscope.

7. The external mechanism according to claim 1, further comprising a transmission comprising:
   a switching gear; and
   a switching tab configured to move the switching gear in an axial direction of a switching gear shaft.

8. The external mechanism according to claim 7, wherein
   the one or more first protrusions comprise a meshing portion including a gear on an outer peripheral surface,
   the actuator comprising a driving gear disposed on a shaft of the actuator, and
   the switching gear is configured to be meshed with the gear and the driving gear.

9. The external mechanism according to claim 7, wherein the housing case comprising:
   a first through hole in which the switching tab is disposed; and
   a second through hole in which a bending state display portion is disposed, the bending state display portion rotating in a same direction following rotation of the one or more first protrusions.

10. The external mechanism according to claim 1, wherein the operation switch is a slide switch.

11. The external mechanism according to claim 1, wherein the operation switch is a seesaw switch.

12. The external mechanism according to claim 1,
   wherein the one or more second protrusions include a groove,
   wherein the one or more second recesses include a holding claw configured to elastically deform and engage the groove.

13. The external mechanism according to claim 1, wherein the one or more second recesses includes a locking piece and a biasing material abutting on and biasing a side surface of the locking piece.

14. The external mechanism according to claim 1, wherein the first and second contact surfaces are configured to be flat.

* * * * *